United States Patent
Choi et al.

(10) Patent No.: US 7,034,096 B2
(45) Date of Patent: Apr. 25, 2006

(54) RING-EXPANSION OF CYCLIC OLEFINS METATHESIS REACTIONS WITH AN ACYCLIC DIENE

(75) Inventors: Tae-Lim Choi, Pasadena, CA (US); Choon Woo Lee, Pasadena, CA (US); Hyunjin M. Kim, San Ramon, CA (US); Robert H. Grubbs, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/371,196

(22) Filed: Feb. 19, 2003

(65) Prior Publication Data

US 2003/0236367 A1 Dec. 25, 2003

Related U.S. Application Data

(60) Provisional application No. 60/359,055, filed on Feb. 19, 2002.

(51) Int. Cl.
*C08F 4/44* (2006.01)
*B01J 31/38* (2006.01)

(52) U.S. Cl. ............. 526/336; 526/171; 526/172; 502/152; 502/155

(58) Field of Classification Search ............ 526/171, 526/172, 336; 502/152, 155
See application file for complete search history.

(56) References Cited

U.S. PATENT DOCUMENTS

| 5,731,383 | A |   | 3/1998 | Nubel et al. |
| 5,750,815 | A | * | 5/1998 | Grubbs et al. ............ 585/511 |
| 6,107,237 | A |   | 8/2000 | Wagener et al. |
| 6,111,121 | A |   | 8/2000 | Grubbs et al. |

FOREIGN PATENT DOCUMENTS

| WO | WO 02/079126 | 10/2002 |
| WO | WO 02/079127 | 10/2002 |
| WO | WO 02/079208 | 10/2002 |

OTHER PUBLICATIONS

Grubbs et al., Ring Expansion via Olefin Metathesis, JACS, 2002, 124, 3224-3225.*
International Search Report, PCT/US03/05207, Jun. 02, 2003.

Scherman, Oren A., "Synthesis of Well-Defined Poly((vinyl alcohol)$_2$-alt-methylene) via Ring-Opening Metathesis Polymerization", *Macromolecules*, 2002, vol. 35, No. 14, pp. 5366-5371.

Lee, Choon Woo et al, "Ring Expansion via Olefin Metathesis", *J. Am. Chem. Soc.*, 2002, vol. 124, No. 13, pp. 3224-3225.

Choi, Tae-Lim et al, "Synthesis of A,B-Alternating Copolymers by Ring-Opening-Insertion-Metathesis Polymerization", *Angew. Chem. Intl. Ed.*, 2002, vol. 41, No. 20, pp. 3839-3841.

Schultz, Laura G. et al, "Synthesis of Cored Dendrimers with Internal Cross-Links", *Angew. Chem. Intl. Ed.*, 2001, vol. 40, No. 10, pp. 1962-1966.

Lee, Choon Woo et al, "Formation of Macrocycles via Ring-Closing Olefin Metathesis", *J. Org Chem.*, 2001, vol. 66, 7155-7158.

Fürstner, Alois, "Exploiting the Reversibility of Olefin Metathesis. Synthesis of Macrocyclic Trisubstituted Alkenes and (R,R)-(-)-Pyrenophorin", *Org. Lett.*, 2001, vol. 3, No. 3, pp. 449-451.

Garbaccio, Robert M. et al, "Efficient Asymmetric Synthesis of Radicol Dimethyl Ether: A Novel Application of Ring-Forming Olefin Metathesis", *Org. Lett.*, 2000, vol. 2, No. 20, pp. 3127-3129.

Lee, Choon Woo et al, "Stereoselectivity of Macrocyclic Ring-Closing Olefin Metathesis", *Org. Lett.*, 2000, vol. 2, No. 14, 2145-2147.

Roxburgh, Craig J., "The Synthesis of Large-Ring Compounds", *Tetrahedron*, 1995, vol. 51, No. 36, pp. 9767-9822.

* cited by examiner

*Primary Examiner*—Robert D. Harlan
(74) *Attorney, Agent, or Firm*—Reed IP Law Group

(57) ABSTRACT

This invention relates generally to synthetic procedures that include the step of ring-opening metathesis of cyclic olefins and reaction with an acyclic diene co-reactant to produce olefin macrocycles by ring expansion, or alternatively. The ring expansion of the cyclic olefin is provided by three types of sequential olefin metathesis (ring-opening, cross, and ring-closing olefin metathesis). More particularly, the invention pertains to synthesis of olefin macrocycles via olefin metathesis reactions using a Group 8 transition metal complex as the metathesis catalyst. Macrocycles provided herein have a variety of uses in the pharmaceutical, biomedical, organic synthesis and chemical industries, such as the production of crown ethers that are useful as metal complexing species.

47 Claims, No Drawings

US 7,034,096 B2

RING-EXPANSION OF CYCLIC OLEFINS METATHESIS REACTIONS WITH AN ACYCLIC DIENE

CROSS-REFERENCE TO RELATED APPLICATIONS

This application claims priority under 35 U.S.C. § 119(e)(1) to Provisional U.S. Patent Application Ser. No. 60/359,055, filed Feb. 19, 2002. The disclosure of the aforementioned application is incorporated by reference in its entirety.

ACKNOWLEDGEMENT OF GOVERNMENT SUPPORT

The U.S. Government has certain rights in this invention pursuant to Grant No. CHE-9809856 awarded by the National Science Foundation.

TECHNICAL FIELD

This invention relates generally to the use of olefin metathesis in the synthesis of polymers, and more particularly relates to the synthesis of olefin macrocycles olefin metathesis reactions using a Group 8 transition metal complex as the metathesis catalyst. Macrocycles provided herein have a variety of uses in the pharmaceutical, biomedical, organic synthesis and chemical industries, such as the production of crown ethers that are useful as metal complexing species.

BACKGROUND OF THE INVENTION

Olefin metathesis is an efficient reaction for the formation of carbon-carbon bonds by exchanging substituent groups on two olefin reactants. Certain ruthenium catalysts have helped to increase the practicality of using olefin metathesis for organic synthesis due to modified functional groups that have increased their tolerance to air and moisture. However, highly active catalysts can be sensitive to some polar functional groups, while catalysts that are more highly stable to polar functional groups can have diminished activity. Therefore, improved catalysts that are more highly stable to functional groups while retaining substantially undiminished activity are needed, as well as improved processes that can utilize such catalysts. More active and more stable catalysts would broaden the practical utility of olefin metathesis use for organic synthesis, e.g., ring-closing and cross metathesis reactions of functionalized olefins using α,β-unsaturated carbonyl compounds.

I. Olefin Macrocyles and Derivatives

One field of organic synthesis that could benefit from improved yields using improved metathesis catalysts is the field of macrocyclization of olefins (and optional subsequent reaction or reduction of the double bonds), which is considered much more difficult than macro-lactonization and macro-lactamization. There is a need for an improved mild and efficient route for the production of carbocycles, particularly ring expansion of cyclic olefins without excessive side reactions, such as polymerization. U.S. Pat. No. 6,482,908 provides a method for producing olefin macrocycles from acyclic diene starting materials (such non-cyclic diene starting materials may be polymeric) by using ring-closing metathesis ("RCM"). Such RCM improved procedures addressed a problem in the art that had required the acyclic diene starting materials to be conformationally restrained in order to achieve acceptable yields. While overcoming some prior art problems, such a process did not provide a method for expanding existing cyclic olefins.

Macrocyclic compounds, such as cyclized olefins or functionalized cyclic molecules are important classes of compounds that are used extensively in the chemical industry, e.g., as metal-complexing species, or as cyclic alcohols for forming esters from organic acids to remove organic acids from solutions. These molecules have many uses including analytical chemistry titrations, forming esters, removal of ions from solutions and soils, iron binding in hemoglobin, magnesium binding in chlorophyll, and for medicinal uses such as antimicrobial agents against gram-positive bacteria, fungi, viruses and the like. One particularly useful class of functionalized cyclic molecules is crown ethers which also find important uses as solubilizers for metals in organic transformation reactions. See Crown Ethers and Analogs, Patai, S. and Rappoport, Z. Eds; John Wiley & Sons: New York, 1989, which is incorporated herein by reference and contains many examples of technically and scientifically important functionalized cyclic molecules including crown-ethers, crown-thioethers, porphyrins, lariats, cryptands, sandwich complexes and the like.

When the functionalized cyclic molecules contain a site of unsaturation, as in the case of functionalized cyclic olefins, the site of unsaturation may be used for further chemical modification of the molecule. Such modifications by include chemical addition reactions with the unsaturated bonds or by hydrogenation of the double bond. Carbonyl functional groups may be by reduction to alcohols that are capable of forming esters with acid groups. In addition, cyclic olefins may contain hetero atoms, e.g. ethers or amine groups. Also, the functionalized cyclic olefins may also be used as the starting materials for polymer or oligomer synthesis via a ring opening metathesis polymerization ("ROMP") reaction. This is discussed further below, since ROMP of such functionalized cyclic olefins can provide an improved method for synthesizing functionalized polymers or oligomers which possess regularly spaced sites of unsaturation and regularly spaced functional groups.

There remains a need for new, improved or larger macrocycles, as well as improved methods (mild and efficient routes) for producing them, such as by a reliable and efficient olefin ring expansion process. But, such a process presents several formidable obstacles that must be overcome before achieving success. For example, cyclic olefins (e.g., cycloalkenes) must be able to undergo a ring-opening metathesis ("ROM") reaction. Once opened, a cycloalkene must react selectively with an acyclic diene for cross metathesis ("CM") to properly occur, and then must undergo a subsequent selective ring closure metathesis ("RCM"). Prior to the present invention such difficulties had not been overcome.

II. Transition Metal Carbene Complexes as Metathesis Catalysts

Transition metal carbene complexes, particularly ruthenium and osmium carbene complexes, have been described as metathesis catalysts in U.S. Pat. Nos. 5,312,940, 5,342,909, 5,831,108, 5,969,170, 6,111,121, and 6,211,391 to Grubbs et al., assigned to the California Institute of Technology. The ruthenium and osmium carbene complexes disclosed in these patents all possess metal centers that are formally in the +2 oxidation state, have an electron count of 16, and are penta-coordinated. Such complexes have been disclosed as useful in catalyzing a variety of olefin metathesis reactions, including ROMP, ring closing metathesis ("RCM"), acyclic diene metathesis polymerization ("ADMET"), ring-opening metathesis ("ROM"), and cross-metathesis ("CM" or "XMET") reactions. Examples of such catalysts are $(PCy_3)_2(Cl)_2Ru=CHPh$ (1) and $(IMesH_2)(PCy_3)(Cl)_2Ru=CHPh$ (2):

1:

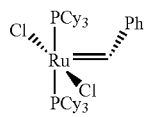

2:

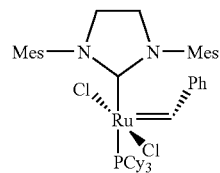

In the above molecular structures, "Mes" represents mesityl (2,4,6-trimethylphenyl), "Ph" is phenyl, and "Cy" is cyclohexyl.

Accordingly, there is a need in the art for improved methods of synthesizing olefin macrocycles and their derivatives using catalysts that are tolerant of functional groups and a process that enables precise controls over the resulting products and structural distribution of functional groups in the molecules produced. Ideally, such method would also be useful in the synthesis of novel olefin macrocycles. The invention is directed to such methods, and now provides a highly effective process using a transition metal carbene complex such as (1) or (2). The processes can be used to synthesize expanded olefin macrocycles, in a manner that enables careful control over the macrocycles produced and their properties, as well as derivatives thereof.

SUMMARY OF THE INVENTION

The invention is directed, in part, to a method for synthesizing a macrocycle by ring expansion of a cyclic olefin, comprising three metathesis steps in the following order:

(i) a ring-opening metathesis (ROM) reaction step of the cyclic olefin;

(ii) a cross metathesis (CM) step reaction with a diene having two terminal olefinic groups; and (iii) a ring closure metathesis (RCM) reaction step;

(iii) a ring closure metathesis (RCM) reaction step;

wherein steps (i)–(iii) are carried out in the present of a catalytically effective amount of an olefin metathesis catalyst under reaction conditions effective to allow each of the three metathesis reactions to occur.

The olefin metathesis catalyst for carrying out the aforementioned polymerization reaction is preferably a Group 8 transition metal complex having the structure of formula (I)

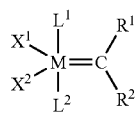

in which:

M is a Group 8 transition metal;

$L^1$ and $L^2$ are neutral electron donor ligands;

$X^1$ and $X^2$ are anionic ligands; and $R^1$ and $R^2$ are independently selected from hydrogen, hydrocarbyl, substituted hydrocarbyl, heteroatom-containing hydrocarbyl, substituted heteroatom-containing hydrocarbyl, and functional groups, wherein any two or more of $X_1$, $X^2$, $L^1$, $L^2$, $R^1$, and $R^2$ can be taken together to form a cyclic group, and further wherein any one or more of $X^1$, $X^2$, $L^1$, $L^2$, $R^1$, and $R^2$ may be attached to a support.

Preferred catalysts contain Ru or Os as the Group 8 transition metal, with Ru particularly preferred.

The catalysts having the structure of formula (1) are in one of two groups. In the first group, $L^1$ and $L^2$ are independently selected from phosphine, sulfonated phosphine, phosphite, phosphinite, phosphonite, arsine, stibine, ether, amine, amide, imine, sulfoxide, carboxyl, nitrosyl, pyridine, substituted pyridine, imidazole, substituted imidazole, pyrazine, and thioether. Exemplary ligands are trisubstituted phosphines. The first group of catalysts, accordingly, is exemplified by the ruthenium bisphosphine complex $(PCy_3)_2 (Cl)_2Ru=CHPh$ (1)

1:

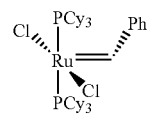

The catalysts of the second group are transition metal carbene complexes, preferably ruthenium carbene complexes, wherein $L^2$ is as defined above and $L^1$ is a carbene having the structure of formula (II)

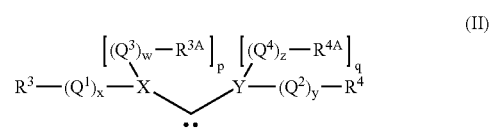

(II)

such that the complex has the structure of formula (IIA)

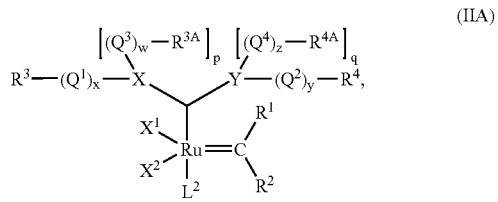

(IIA)

wherein:

$X^1$, $X^2$, $L^1$, $L^2$, $R^1$, and $R^2$ are as defined above;

X and Y are heteroatoms selected from N, O, S, and P;

p is zero when X is O or S, and p is 1 when X is N or P;

q is zero when Y is O or S, and q is 1 when Y is N or P;

$Q^1$, $Q^2$, $Q^3$, and $Q^4$ are independently selected from hydrocarbylene, substituted hydrocarbylene, heteroatom-containing hydrocarbylene, substituted heteroatom-containing hydrocarbylene, and —(CO)—, and further wherein two or more substituents on adjacent atoms within Q may be linked to form an additional cyclic group;

w, x, y, and z are independently zero or 1; and $R^3$, $R^{3A}$, $R^4$, and $R^{4A}$ are independently selected from hydrogen, hydrocarbyl, substituted hydrocarbyl, heteroatom-containing hydrocarbyl, and substituted heteroatom-containing hydrocarbyl, wherein any two or more of $X^1$, $X^2$, $L^2$, $R^1$, $R^2$, $R^3$, $R^{3A}$, $R^4$, and $R^{4A}$ can be taken together to form a cyclic group, and further wherein any one or more of $X^1$, $X^2$, $L^2$, $R^1$, $R^2$, $R^3$, $R^{3A}$, $R^4$, and $R^{4A}$ may be attached to a support.

The second group of catalysts, accordingly, is exemplified by the ruthenium carbene complex $(IMesH_2)(PCy_3)(Cl)_2Ru=CHPh$ (2):

2:

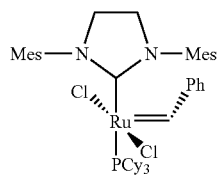

Additional transition metal carbene complexes useful as catalysts in conjunction with the present invention include, but are not limited to, neutral ruthenium or osmium metal carbene complexes containing metal centers that are formally in the +2 oxidation state, have an electron count of 16, are penta-coordinated, and are of the general formula (IIIA). Other preferred metathesis catalysts include, but are not limited to, cationic ruthenium or osmium metal carbene complexes containing metal centers that are formally in the +2 oxidation state, have an electron count of 14, are tetra-coordinated, and are of the general formula (IIIB). Still other preferred metathesis catalysts include, but are not limited to, neutral ruthenium or osmium metal carbene complexes containing metal centers that are formally in the +2 oxidation state, have an electron count of 18, are hexa-coordinated, and are of the general formula III(C).

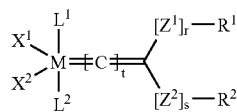
(IIIA)

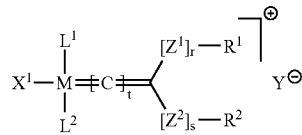
(IIIB)

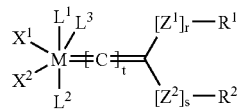
(IIIC)

In the foregoing structures, $X^1$, $X^2$, $L^1$, $L^2$, $R^1$, and $R^2$ are as defined previously, r and s are independently zero or 1, t is an integer in the range of zero to 5, Y is any noncoordinating anion, $Z^1$ and $Z^2$ are independently selected from —O—, —S—, —NR$^2$—, —PR$^2$—, —P(=O)R$^2$—, —P(OR$^2$)—, —P(=O)(OR$^2$)—, —C(=O)—, —C(=O)O—, —OC(=O)—, —OC(=O)O—, —S(=O)—, or —S(=O)$_2$—, and any two or more of $X^1$, $X^2$, $L^1$, $L^2$, $Z^1$, $Z^2$, $R^1$, and $R^2$ may be taken together to form a cyclic group, e.g., a multidentate ligand, and wherein any one or more of $X^1$, $X^2$, $L^1$, $L^2$, $Z^1$, $Z^2$, $R^1$, and $R^2$ may be attached to a support.

The cyclic olefin monomer has the structure of formula (IV)

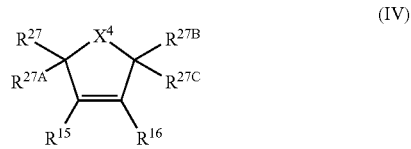
(IV)

wherein:

$X^4$ is a one-atom to five-atom linkage (with a "one-atom" linkage referring to a linkage that provides a single, optionally substituted spacer atom between the two adjacent carbon atoms, and a "five-atom" linkage, similarly, referring to a linkage that provides five optionally substituted spacer atoms between the two adjacent carbon atoms);

one of $R^{15}$ and $R^{16}$ is hydrogen and the other is selected from hydrogen, hydrocarbyl (e.g., $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, and $C_6$–$C_{24}$ aralkyl), substituted hydrocarbyl (e.g., substituted $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, and $C_6$–$C_{24}$ aralkyl), heteroatom-containing hydrocarbyl (e.g., heteroatom-containing $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, and $C_6$–$C_{24}$ aralkyl), substituted heteroatom-containing hydrocarbyl (e.g., substituted heteroatom-containing $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, and $C_6$–$C_{24}$ aralkyl), and -(L)$_v$-Fn wherein v is zero or 1, L is hydrocarbylene, substituted hydrocarbylene and/or heteroatom-containing hydrocarbylene, and Fn is a protected or unprotected functional group; and $R^{27}$, $R^{27A}$, $R^{27B}$, and $R^{27C}$ are independently selected from hydrogen, hydrocarbyl, substituted hydrocarbyl, heteroatom-containing hydrocarbyl, and substituted heteroatom-containing hydrocarbyl, and -(L)$_v$-Fn, and further wherein any two of $R^{27}$, $R^{27A}$, $R^{27B}$, and $R^{27C}$ may be taken together to form a cyclic structure, such that the olefin monomer is bicyclic, with the proviso that when the olefin monomer is bicyclic, then $X^4$ is a one-atom or two-atom linkage.

In one preferred embodiment, $R^{27A}$ and $R^{27C}$ are hydrogen, $R^{27}$ is -(L)$_v$-Fn wherein v is zero and -Fn is —$X^{3A}$—(R$^{18}$)$_n$, and $R^{27B}$ is -(L)$_n$-Fn wherein v is zero and -Fn is —$X^3$—(R$^{17}$)$_m$, and further wherein $X^3$ and $X^{3A}$ are directly or indirectly linked, in which case the cyclic olefin monomer has the structure of formula (VII)

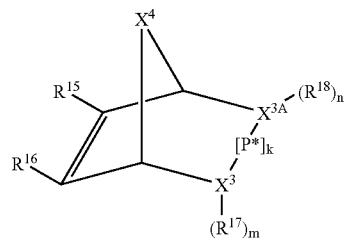
(VII)

in which:

$X^4$ is a one-atom or two-atom linkage;

$R^{15}$, and $R^{16}$ are as defined above;
$X^3$ and $X^{3A}$ are independently N, O, or S;
k is zero or 1;
m and n are independently zero or 1;
P* is a heteroatom-protecting group;
$R^{17}$ and $R^{18}$ are independently selected from hydrogen, hydrocarbyl, substituted hydrocarbyl, heteroatom-containing hydrocarbyl, substituted heteroatom-containing hydrocarbyl, and amino protecting groups, wherein $R^{17}$ and $R^{18}$ may be taken together to form a cyclic group, with the provisos that:
when $X^3$ is O or S, then m is zero;
when $X^{3A}$ is O or S, then n is zero;
when $X^3$ is N, then m is 1; and
when $X^{3A}$ is N, then n is 1.

In another preferred embodiment, $R^{27A}$ and $R^{27C}$ of formula (IV) are hydrogen, in which case the cyclic olefin has the structure of formula (VIIa)

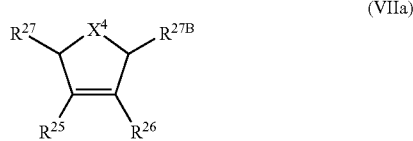

(VIIa)

wherein $X^4$, $R^{27}$, and $R^{27B}$ are as defined previously, and $R^{25}$ and $R^{26}$ are defined as for $R^{15}$ and $R^{16}$.

The invention also provides, as novel compositions of matter, expanded cyclic olefin macrocycles that are synthesized using the methodology of the invention. The macrocycles are saturated or unsaturated, and, in a first embodiment, are comprised of residues having the structure of formula (XV) corresponding to the cyclic olefin monomer absent its olefin (c=c) portion that has been replaced with a structure of either formula (XVa) or (XVb) corresponding to the diene having two terminal olefinic groups.

The invention also provides a method for synthesizing such microcycles by ring expansion of a cyclic olefin with a diene monomer having two terminal olefinic groups, wherein the cyclic olefin is as described above and the diene monomer is as described above, and the two starting materials are reacted at a concentration of the diene monomer which is about 50 to 150 times more dilute than the concentration of diene that would be utilized for a ROMP/ROIMP polymerization process, as described in greater detail below.

The invention provides a method for synthesizing a macrocycle by ring expansion of a cyclic olefin, comprising three metathesis steps in the following order:
(i) a ring-opening metathesis (ROM) reaction step of the cyclic olefin,
(ii) a cross metathesis (CM) step reaction with a diene having two terminal olefinic groups, and
(iii) a ring closure metathesis (RCM) reaction step;
wherein steps (i)–(iii) are carried out in the present of a catalytically effective amount of an olefin metathesis catalyst under reaction conditions effective to allow each of the three metathesis reactions to occur.

More details and examples for producing macrocycles by ring expansion are set forth below.

DETAILED DESCRIPTION OF THE INVENTION

I. Definitions and Nomenclature:

It is to be understood that unless otherwise indicated this invention is not limited to specific reactants, reaction conditions, ligands, metal complexes, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a compound" encompasses a combination or mixture of different compounds as well as a single compound, reference to "a substituent" includes a single substituent as well as two or more substituent groups that may or may not be the same, and the like.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

The term "alkyl" as used herein refers to a linear, branched, or cyclic saturated hydrocarbon group typically although not necessarily containing 1 to about 20 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups, herein contain 1 to about 12 carbon atoms. The term "lower alky" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl-and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 20 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 20 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 20 carbon atoms and either one aromatic ring or 2 to 4 fused or linked aromatic rings, e.g., phenyl, naphthyl, biphenyl, and the like, with more preferred aryl groups containing 1 to 3 aromatic rings, and particularly preferred aryl groups containing 1 or 2 aromatic rings and 5 to 14 carbon atoms. "Substituted aryl" refers to an aryl moiety substituted with one or more substituent groups, and the terms "heteroatom-containing aryl" and "heteroaryl" refer to aryl in which at least one carbon atom is replaced with a heteroatom. Unless otherwise indicated, the terms "aromatic," "aryl," and "arylene" include heteroaromatic, substituted aromatic, and substituted heteroaromatic species.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 20 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctyl-naphthyl, 3-ethyl-cyclopenta-1,4-dienyl, and the like.

The terms "halo," "halide," and "halogen" are used in the conventional sense to refer to a chloro, bromo, fluoro, or iodo substituent. The terms "haloalkyl," "haloalkenyl," and "haloalkynyl" (or "halogenated alkyl," "halogenated alkenyl," and "halogenated alkynyl") refer to an alkyl, alkenyl, or alkynyl group, respectively, in which at least one of the hydrogen atoms in the group has been replaced with a halogen atom.

"Hydrocarbyl" refers to univalent hydrocarbyl radicals containing 1 to about 30 carbon atoms, preferably 1 to about 20 carbon atoms, more preferably 1 to about 12 carbon atoms, including linear, branched, cyclic, saturated, and unsaturated species, such as alkyl groups, alkenyl groups, aryl groups, and the like. The term "lower hydrocarbyl" intends a hydrocarbyl group of 1 to 6 carbon atoms, and the term "hydrocarbylene" intends a divalent hydrocarbyl moiety containing 1 to about 30 carbon atoms, preferably 1 to about 20 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. Unless otherwise indicated, the terms "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage, or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, inudazolyl, 1,2,4-triazolyl, tetrazolyl, etc., and examples of heteroatom-containing alicyclic groups are pyrrolidino, morpholino, piperazino, piperidino, etc. It should be noted that a "heterocyclic" group or compound may or may not be aromatic, and further that "heterocycles" may be monocyclic, bicyclic, or polycyclic as described above with respect to the term "aryl."

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with a non-hydrogen substituent. Examples of such substituents include, without limitation, functional groups such as halide, hydroxyl, sulfhydryl, $C_1$–$C_{20}$ alkoxy, $C_2$–$C_{20}$ alkenyloxy, $C_2$–$C_{20}$ alkynyloxy, $C_5$–$C_{20}$ aryloxy, $C_2$–$C_{20}$ acyl (including $C_2$–$C_{20}$ alkylcarbonyl (—CO-alkyl) and $C_6$–$C_{20}$ arylcarbonyl (—CO-aryl)), acyloxy (—O-acyl), $C_2$–$C_{20}$ alkoxycarbonyl (—(CO)—O-alkyl), $C_6$–$C_{20}$ aryloxycarbonyl (—(CO)—O-aryl), halocarbonyl (—CO)—X where X is halo), $C_2$–$C_{20}$ alkyl-carbonato (—O—(CO)—O-alkyl), $C_6$–$C_{20}$ arylcarbonato (—O—(CO)—O-aryl), carboxy (—COOH), carboxylato (—COO⁻), carbamoyl (—(CO)—NH$_2$), mono-($C_1$–$C_{20}$ alkyl)-substituted carbamoyl (—(CO)—NH ($C_1$–$C_{20}$ alkyl)), di-($C_1$–$C_{20}$ alkyl)-substituted carbamoyl (—(CO)—N($C_1$–$C_{20}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—C≡N), cyanato (—O—C≡N), formyl (—(CO)—H), thioformyl (—(CS)—H), amino (—NH$_2$), mono- and di-($C_1$–$C_{20}$ alkyl)-substituted amino, mono- and di-($C_5$–$C_{20}$ aryl)-substituted amino, $C_2$–$C_{20}$ alkylamido (—NH—(CO)-alkyl), $C_6$–$C_{20}$ arylamido (—NH—(CO)-aryl), imino (—CR=NH where R=hydrogen, $C_1$–$C_{20}$ alkyl, $C_5$–$C_{20}$ aryl, $C_6$–$C_{24}$ alkaryl, $C_6$–$C_{24}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O⁻), $C_1$–$C_{20}$ alkylsulfanyl (—S-alkyl; also termed "alkylthio"), arylsulfanyl (—S-aryl; also termed "arylthio"), $C_1$–$C_{20}$ alkylsulfinyl (—(SO)-alkyl), $C_5$–$C_{20}$ arylsulfinyl (—(SO)-aryl), $C_1$–$C_{20}$ alkylsulfonyl (—SO$_2$-alkyl), $C_5$–$C_{20}$ arylsulfonyl (—SO$_2$-aryl), thiocarbonyl (=S), boryl (—BH$_2$), borono (—B(OH)$_2$), boronato (—B(OR)$_2$ where R is alkyl or other hydrocarbyl), phospho (—PO$_2$), phosphino (—PH$_2$), silyl (—SiR$_3$ wherein R is hydrogen or hydrocarbyl), silyloxy (—O-silyl), silanyl (—NR-silyl, where R is hydrogen or hydrocarbyl), stannyl, or germyl; and the hydrocarbyl moieties $C_1$–$C_{20}$ alkyl (preferably $C_1$–$C_{18}$ alkyl, more preferably $C_1$–$C_{12}$ alkyl, most preferably $C_1$–$C_6$ alkyl), $C_2$–$C_{20}$ alkenyl (preferably $C_2$–$C_{18}$ alkenyl, more preferably $C_2$–$C_{12}$ alkenyl, most preferably $C_2$–$C_6$ alkenyl), $C_2$–$C_{20}$ alkynyl (preferably $C_2$–$C_{18}$ alkynyl, more preferably $C_2$–$C_{12}$ alkynyl, most preferably $C_2$–$C_6$ alkynyl), $C_5$–$C_{20}$ aryl (preferably $C_5$–$C_{14}$ aryl), $C_6$–$C_{24}$ alkaryl (preferably $C_6$–$C_{18}$ alkaryl), and $C_6$–$C_{24}$ aralkyl (preferably $C_6$–$C_{18}$ aralkyl).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Analogously, the term "optionally substituted alkyl, alkenyl and alkynyl" is to be interpreted as "optionally substituted alkyl, optionally substituted alkenyl and optionally substituted alkynyl," and a "bridged bicyclic or polycyclic olefin monomer" is to be interpreted as a "bridged bicyclic olefin monomer" or a "bridged polycyclic olefin monomer."

The term "regioregular polymer" is used to refer to a polymer with a regular arrangement of the "connectivity" between the monomer units.

The term "regioregular copolymer" is used to refer the connectivity of monomeric units (e.g., monomeric unit A and monomeric unit B) along the polymeric backbone wherein the copolymer is composed of the two connected in a regularly alternating arrangement pattern ( . . . ABABAB . . . ) along its polymeric backbone. In one preferred type of regioregular copolymer each of the two monomeric units is also symmetrical along a central axis of the monomer unit the "connectivity" between the monomer units The term "telechelic" is used in the conventional sense to refer to a macromolecule, e.g., a polymer or copolymer, that is capped by at least one reactive end group. Preferred telechelic compounds herein are regioregular copolymers having two terminal functional groups each capable of undergoing further reaction.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

In the molecular structures herein, the use of bold and dashed lines to denote particular conformation of groups follows the IUPAC convention. A bond indicated by a broken line indicates that the group in question is below the general plane of the molecule as drawn (the "α" configuration), and a bond indicated by a bold line indicates that the group at the position in question is above the general plane of the molecule as drawn (the "β" configuration).

II. Catalysts:

The metathesis reactions of the invention are carried out catalytically, using a Group 8 transition metal complex as the catalyst. These transition metal carbene complexes include a metal center in a +2 oxidation state, have an electron count of 16, and are penta-coordinated. The complexes are represented by the structure of formula (I)

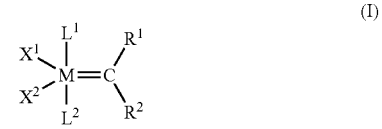

(I)

wherein the various substituents are as follows:

M, which serves as the transition metal center in the +2 oxidation state, is a Group 8 transition metal, particularly ruthenium or osmium. In a particularly preferred embodiment, M is ruthenium.

$X^1$ and $X^2$ are anionic ligands, and may be the same or different, or are linked together to form a cyclic group, typically although not necessarily a five- to eight-membered ring. In preferred embodiments, $X^1$ and $X^2$ are each independently hydrogen, halide, or one of the following groups: $C_1$–$C_{20}$ alkyl, $C_5$–$C_{20}$ aryl, $C_1$–$C_{20}$ alkoxy, $C_5$–$C_{20}$ aryloxy, $C_2$–$C_{20}$ alkoxy-carbonyl, $C_6$–$C_{20}$ aryloxycarbonyl, $C_2$–$C_{20}$ acyl, $C_2$–$C_{20}$ acyloxy, $C_1$–$C_{20}$ alkylsulfonato, $C_5$–$C_{20}$ arylsulfonato, $C_1$–$C_{20}$ alkylsulfanyl, $C_5$–$C_{20}$ arylsulfanyl, $C_1$–$C_{20}$ alkylsulfinyl, or $C_5$–$C_{20}$ arylsulfinyl. Optionally, $X^1$ and $X^2$ may be substituted with one or more moieties selected from $C_1$–$C_{12}$ alkyl, $C_1$–$C_{12}$ alkoxy, $C_5$–$C_{20}$ aryl, and halide, which may, in turn, with the exception of halide, be further substituted with one or more groups selected from halide, $C_1$–$C_6$ alkyl, $C_1$–$C_6$ alkoxy, and phenyl. In more preferred embodiments, $X^1$ and $X^2$ are halide, benzoate, $C_2$–$C_6$ acyl, $C_2$–$C_6$ alkoxycarbonyl, $C_1$–$C_6$ alkyl, phenoxy, $C_1$–$C_6$ alkoxy, $C_1$–$C_6$ alkylsulfanyl, aryl, or $C_1$–$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, (CF$_3$)$_2$(CH$_3$)CO, (CF$_3$)(CH$_3$)$_2$CO, PhO, MeO, EtO, tosylate, mesylate, or trifluoromethane-sulfonate. In the most preferred embodiments, X$^1$ and X$^2$ are each chloride.

R$^1$ and R$^2$ are independently selected from hydrogen, hydrocarbyl (e.g., C$_1$–C$_{20}$ alkyl, C$_2$–C$_{20}$ alkenyl, C$_2$–C$_{20}$ alkynyl, C$_5$–C$_{20}$ aryl, C$_6$–C$_{24}$ alkaryl, C$_6$–C$_{24}$ aralkyl, etc.), substituted hydrocarbyl (e.g., substituted C$_1$–C$_{20}$ alkyl, C$_2$–C$_{20}$ alkenyl, C$_2$–C$_{20}$ alkynyl, C$_5$–C$_{20}$ aryl, C$_6$–C$_{24}$ alkaryl, C$_6$–C$_{24}$ aralkyl, etc.), heteroatom-containing hydrocarbyl (e.g., heteroatom-containing C$_1$–C$_{20}$ alkyl, C$_2$–C$_{20}$ alkenyl, C$_2$–C$_{20}$ alkynyl, C$_5$–C$_{20}$ aryl, C$_6$–C$_{24}$ alkaryl, C$_6$–C$_{24}$ aralkyl, etc.), and substituted heteroatom-containing hydrocarbyl (e.g., substituted heteroatom-containing C$_1$–C$_{20}$ alkyl, C$_2$–C$_{20}$ alkenyl, C$_2$–C$_{20}$ alkynyl, C$_5$–C$_{20}$ aryl, C$_6$–C$_{24}$ alkaryl, C$_6$–C$_{24}$ aralkyl, etc.), and functional groups. R$^1$ and R$^2$ may also be linked to form a cyclic group, which may be aliphatic or aromatic, and may contain substituents and/or heteroatoms. Generally, such a cyclic group will contain 4 to 12, preferably 5 to 8, ring atoms. R$^1$ and R$^2$ may also together form a vinylidene moiety or an analog thereof, as discussed infra with respect to catalysts having the structure of formula (IIIA).

In preferred catalysts, the R$^1$ substituent is hydrogen and the R$^2$ substituent is selected from C$_1$–C$_{20}$ alkyl, C$_2$–C$_{20}$ alkenyl, and C$_5$–C$_{20}$ aryl. More preferably, R$^2$ is phenyl, vinyl, methyl, isopropyl, or t-butyl, optionally substituted with one or more moieties selected from C$_1$–C$_6$ alkyl, C$_1$–C$_6$ alkoxy, phenyl, and a functional group Fn as defined in part (I) of this section. Still more preferably, R$^2$ is phenyl or vinyl substituted with one or more moieties selected from methyl, ethyl, chloro, bromo, iodo, fluoro, nitro, dimethylamino, methyl, methoxy, and phenyl. In the most preferred embodiments, the R$^2$ substituent is phenyl or —C═C(CH$_3$)$_2$.

L$^1$ and L$^2$ are neutral electron donor ligands. L$^1$ may or may not be linked to R$^1$, and L$^2$ may or may not be linked to R$^2$. Examples of suitable L$^2$ moieties include, without limitation, phosphine, sulfonated phosphine, phosphite, phosphinite, phosphonite, arsine, stibine, ether (including cyclic ethers), amine, amide, imine, sulfoxide, carboxyl, nitrosyl, pyridine, substituted pyridine (e.g., halogenated pyridine), imidazole, substituted imidazole (e.g., halogenated imidazole), pyrazine (e.g., substituted pyrazine), and thioether. In more preferred embodiments, L$^2$ is a phosphine of the formula PR$^5$R$^6$R$^7$, where R$^5$, R$^6$, and R$^7$ are each independently aryl or C$_1$–C$_{10}$ alkyl, particularly primary alkyl, secondary alkyl, or cycloalkyl. In the most preferred embodiments, L$^1$ is tricyclohexylphosphine, tricyclopentylphosphine, triisopropylphosphine, triphenylphosphine, diphenylmethylphosphine, or phenyldimethylphosphine, with tricyclohexylphosphine and tricyclopentylphosphine particularly preferred.

It should be emphasized that any two or more (typically two, three, or four) of X$^1$, X$^2$, L$^1$, L$^2$, R$^1$, and R$^2$ can be taken together to form a cyclic group, as disclosed, for example, in U.S. Pat. No. 5,312,940 to Grubbs et al. When any of X$^1$, X$^2$, L$^1$, L$^2$, R$^1$, and R$^2$ are linked to form cyclic groups, those cyclic groups may be five- or six-membered rings, or may comprise two or three five- or six-membered rings, which may be either fused or linked. The cyclic groups may be aliphatic or aromatic, and may be heteroatom-containing and/or substituted, as explained in part (I) of this section.

The cyclic group may, in some cases, form a bidentate ligand or a tridentate ligand. Examples of bidentate ligands include, but are not limited to, bisphosphines, dialkoxides, alkyldiketonates, and aryldiketonates. Specific examples include —P(Ph)$_2$CH$_2$CH$_2$P(Ph)$_2$—, —As(Ph)$_2$CH$_2$CH$_2$As(Ph$_2$)—, —P(Ph)$_2$CH$_2$CH$_2$C(CF$_3$)$_2$O—, binaphtholate dianions, pinacolate dianions, —P(CH$_3$)$_2$(CH$_2$)$_2$P(CH$_3$)$_2$—, and —OC(CH$_3$)$_2$(CH$_3$)$_2$CO—. Preferred bidentate ligands are —P(Ph)$_2$CH$_2$CH$_2$P(Ph)$_2$— and —P(CH$_3$)$_2$(CH$_2$)$_2$P(CH$_3$)$_2$—. Tridentate ligands include, but are not limited to, (CH$_3$)$_2$ NCH$_2$CH$_2$P(Ph)CH$_2$CH$_2$N(CH$_3$)$_2$. Other preferred tridentate ligands are those in which any three of X$^1$, X$^2$, L$^1$, L$^2$, R$^1$, and R$^2$ (e.g., X$^1$, L$^1$, and L$^2$) are taken together to be cyclopentadienyl, indenyl, or fluorenyl, each optionally substituted with C$_2$–C$_{20}$ alkenyl, C$_2$–C$_{20}$ alkynyl, C$_1$–C$_{20}$ alkyl, C$_5$–C$_{20}$ aryl, C$_1$–C$_{20}$ alkoxy, C$_2$–C$_{20}$ alkenyloxy, C$_2$–C$_{20}$ alkynyloxy, C$_5$–C$_{20}$ aryloxy, C$_2$–C$_{20}$ alkoxycarbonyl, C$_1$–C$_{20}$ alkylthio, C$_1$–C$_{20}$ alkylsulfonyl, or C$_1$–C$_{20}$ alkylsulfinyl, each of which may be further substituted with C$_1$–C$_6$ alkyl, halide, C$_1$–C$_6$ alkoxy or with a phenyl group optionally substituted with halide, C—C$_6$ alkyl, or C$_1$–C$_6$ alkoxy. More preferably, in compounds of this type, X, L$^1$, and L$^2$ are taken together to be cyclopentadienyl or indenyl, each optionally substituted with vinyl, C$_1$–C$_{10}$ alkyl, C$_5$–C$_{20}$ aryl, C$_1$–C$_{10}$ carboxylate, C$_2$–C$_{10}$ alkoxycarbonyl, C$_1$–C$_{10}$ alkoxy, or C$_5$–C$_{20}$ aryloxy, each optionally substituted with C$_1$–C$_6$ alkyl, halide, C$_1$–C$_6$ alkoxy or with a phenyl group optionally substituted with halide, C$_1$–C$_6$ alkyl or C$_1$–C$_6$ alkoxy. Most preferably, X, L$^1$ and L$^2$ may be taken together to be cyclopentadienyl, optionally substituted with vinyl, hydrogen, methyl, or phenyl. Tetradentate ligands include, but are not limited to O$_2$C(CH$_2$)$_2$P(Ph)(CH$_2$)$_2$P(Ph)(CH$_2$)$_2$CO$_2$, phthalocyanines, and porphyrins.

Complexes wherein L$^2$ and R$^2$ are linked, for example, include the following:

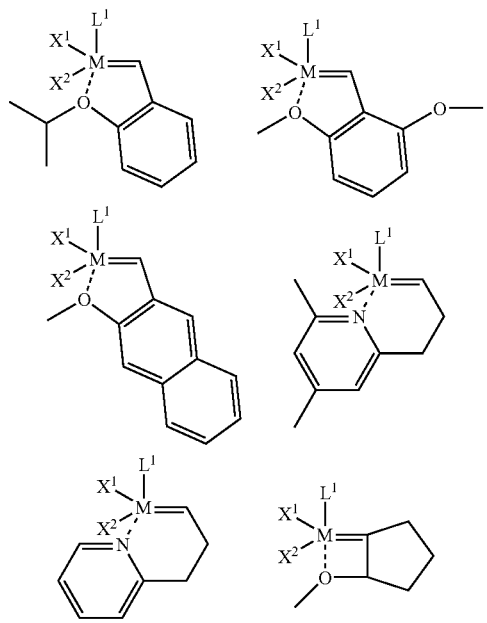

In a first group of catalysts, L$^1$ is as defined for L$^2$, and, in this embodiment, L$^1$ and L$^2$ will generally, although not necessarily, be the same. In these catalysts, L$^1$ and L$^2$ are typically phosphines of the formula PR$^5$R$^6$R$^7$, where R$^5$, R$^6$, and R$^7$ are as defined earlier herein. As above, the most preferred L$^1$ and L$^2$ ligands, in this first catalyst group, are selected from tricyclohexylphosphine, tricyclopentylphosphine, triisopropylphosphine, triphenylphosphine, diphenylmethylphosphine, and phenyldimethylphosphine, with tricyclohexylphosphine and tricyclopentylphosphine particularly preferred. These catalysts are, accordingly, exemplified by ruthenium bisphosphine complexes such as (PCy$_3$)$_2$(Cl)$_2$Ru=CHPh (1).

In a second group of catalysts, the complexes are ruthenium carbene complexes, wherein L$^1$ has the structure of formula (II)

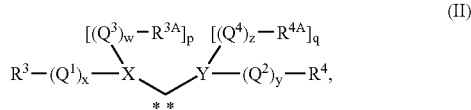

such that the complexes have the structure of formula (IIA)

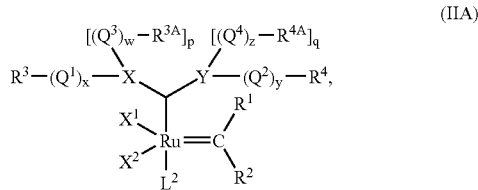

wherein the substituents are as follows:

X and Y are heteroatoms typically selected from N, O, S, and P. Since O and S are divalent, p is necessarily zero when X is O or S, and q is necessarily zero when Y is O or S. However, when X is N or P, then p is 1, and when Y is N or P, then q is 1. In a preferred embodiment, both X and Y are N.

Q$^1$, Q$^2$, Q$^3$, and Q$^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—, and w, x, y, and z are independently zero or 1, meaning that each linker is optional. Preferably, w, x, y, and z are all zero. Further, two or more substituents on adjacent atoms within Q may be linked to form an additional cyclic group.

R$^3$, R$^{3A}$, R$^4$, and R$^{4A}$ are independently selected from hydrogen, hydrocarbyl, substituted hydrocarbyl, heteroatom-containing hydrocarbyl, and substituted heteroatom-containing hydrocarbyl.

In addition, any two or more of X$^1$, X$^2$, L$^2$, R$^1$, R$^2$, R$^3$, R$^{3A}$, R$^4$ and R$^{4A}$ can be taken together to form a cyclic group, and any one or more of X$^1$, X$^2$, L$^2$, R$^1$, R$^2$, R$^3$, R$^{3A}$, R$^4$, and R$^{4A}$ may be attached to a support, as explained above with respect to complexes of formula (I).

Preferably, R$^{3A}$ and R$^{4A}$ are linked to form a cyclic group, such that the complexes of this embodiment have the structure of formula (V)

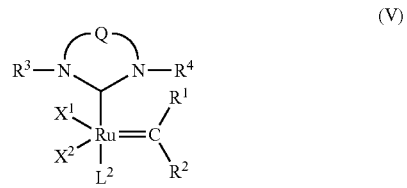

wherein R$^3$ and R$^4$ are defined above, with preferably at least one of R$^3$ and R$^4$, and more preferably both R$^3$ and R$^4$, being alicyclic or aromatic of one to about five rings, and optionally containing one or more heteroatoms and/or substituents. Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to five cyclic groups. Q is often, although again not necessarily, a two-atom linkage or a three-atom linkage, e.g., —CH$_2$—CH$_2$—, —CH(Ph)—CH(Ph)— where Ph is phenyl; =CR—N=, giving rise to an unsubstituted (when R=H) or substituted (R=other than H) triazolyl group; and —CH$_2$—SiR$_2$—CH$_2$— (where R is H, alkyl, alkoxy, etc.).

In a more preferred embodiment, Q is a two-atom linkage having the structure —CR$^8$R$^9$—CR$^{10}$R$^{11}$— or —CR$^8$=CR$^{10}$—, preferably —CR$^8$R$^9$—CR$^{10}$OR$^{11}$, in which case the complex has the structure of formula (Va)

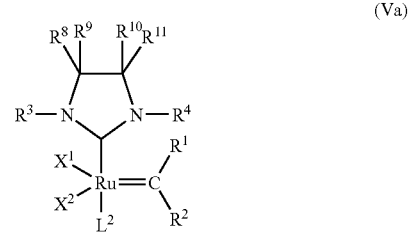

wherein R$^8$, R$^9$, R$^{10}$, and R$^{11}$ are independently selected from hydrogen, hydrocarbyl, substituted hydrocarbyl, heteroatom-containing hydrocarbyl, substituted heteroatom-containing hydrocarbyl, and functional groups as defined in part (I) of this section. Examples of functional groups here include carboxyl, C$_1$–C$_{20}$ alkoxy, C$_5$–C$_{20}$ aryloxy, C$_2$–C$_{20}$ alkoxycarbonyl, C$_2$–C$_{20}$ alkoxycarbonyl, C$_2$–C$_{20}$ acyloxy, C$_1$–C$_{20}$ alkylthio, C$_5$–C$_{20}$ arylthio, C$_1$–C$_{20}$ alkylsulfonyl, and C$_1$–C$_{20}$ alkylsulfinyl, optionally substituted with one or more moieties selected from C$_1$–C$_{10}$ alkyl, C$_1$–C$_{10}$ alkoxy, C$_5$–C$_{20}$ aryl, hydroxyl, sulfhydryl, formyl, and halide. Alternatively, any two of R$^8$, R$^9$, R$^{10}$, and R$^{11}$ may be linked together to form a substituted or unsubstituted, saturated or unsaturated ring structure, e.g., a C$_4$–C$_{12}$ alicyclic group or a C$_5$ or C$_6$ aryl group, which may itself be substituted, e.g., with linked or fused alicyclic or aromatic groups, or with other substituents.

When R$^3$ and R$^4$ are aromatic, they are typically although not necessarily composed of one or two aromatic rings, which may or may not be substituted, e.g., R$^3$ and R$^4$ may be phenyl, substituted phenyl, biphenyl, substituted biphenyl, or the like. In one preferred embodiment, R$^3$ and R$^4$ are the same and have the structure (VI)

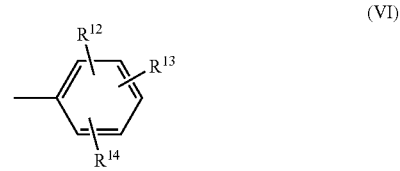

in which $R^{12}$, $R^{13}$, and $R^{14}$ are each independently hydrogen, $C_1$–$C_{20}$ alkyl, substituted $C_1$–$C_{20}$ alkyl, $C_1$–$C_{20}$ heteroalkyl, substituted $C_1$–$C_{20}$ heteroalkyl, $C_5$–$C_{20}$ aryl, substituted $C_5$–$C_{20}$ aryl, $C_5$–$C_{20}$ heteroaryl, $C_5$–$C_{30}$ aralkyl, $C_5$–$C_{30}$ alkaryl, or halide. Preferably, $R^{12}$, $R^{13}$, and $R^{14}$ are each independently hydrogen, $C_1$–$C_{10}$ alkyl, $C_1$–$C_{10}$ alkoxy, $C_5$–$C_{14}$ aryl, substituted $C_5$–$C_{14}$ aryl, or halide. More preferably, $R^3$ and $R^4$ are mesityl, diisopinocamphenyl, or 2,4,2′,6′-tetramethylbiphenylyl, and most preferably, $R^3$ and $R^4$ are mesityl.

Examples of such catalysts include, but are not limited to, the following:

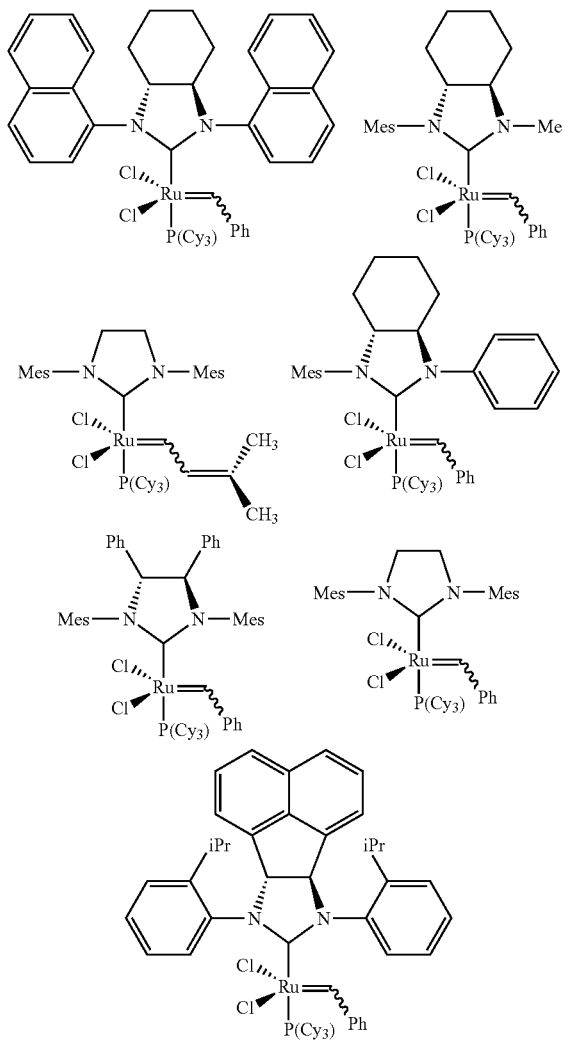

In the foregoing molecular structures, "Mes" represents mesityl (2,4,6-trimethylphenyl), "iPr" is isopropyl, "Ph" is phenyl, and "Cy" is cyclohexyl.

Additional transition metal carbene complexes include, but are not limited to:

neutral ruthenium or osmium metal carbene complexes containing metal centers that are formally in the +2 oxidation state, have an electron count of 16, are penta-coordinated, and are of the general formula (IIIA);

cationic ruthenium or osmium metal carbene complexes containing metal centers that are formally in the +2 oxidation state, have an electron count of 14, are tetra-coordinated, and are of the general formula (IIIB); and neutral ruthenium or osmium metal carbene complexes containing metal centers that are formally in the +2 oxidation state, have an electron count of 18, are hexa-coordinated, and are of the general formula III(C)

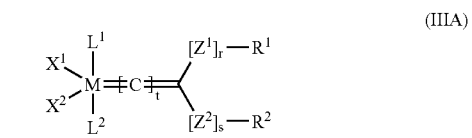

(IIIA)

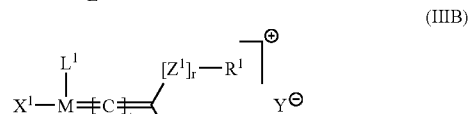

(IIIB)

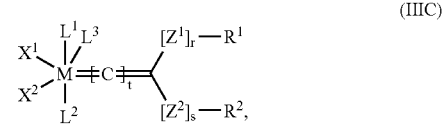

(IIIC)

wherein $X^1$, $X^2$, $L^1$, $L^2$, $R^1$, and $R^2$ are as defined previously, r and s are independently zero or 1, t is an integer in the range of zero to 5, Y is any noncoordinating anion (e.g., a halide ion), $Z^1$ and $Z^2$ are independently selected from —O—, —S—, —$NR^2$—, —$PR^2$—, —P(=O)$R^2$—, —P(O$R^2$)—, —P(=O)(O$R^2$)—, —C(=O)—, —C(=O)O—, —OC(=O)—, —OC(=O)O—, —S(=O)—, or —S(=O)$_2$—, and any two or more of $X^1$, $X^2$, $L^1$, $L^2$, $Z^1$, $Z^2$, $R^1$, and $R^2$ may be taken together to form a cyclic group, e.g., a multidentate ligand, and wherein any one or more of $X^1$, $X^2$, $L^1$, $L^2$, $Z^1$, $Z^2$, $R^1$, and $R^2$ may be attached to a support. As understood in the field of catalysis, suitable solid supports may be of synthetic, semi-synthetic, or naturally occurring materials, which may be organic or inorganic, e.g., polymeric, ceramic, or metallic. Attachment to the support will generally, although not necessarily, be covalent, and the covalent linkage may be direct or indirect, if indirect, typically through a functional group on a support surface.

The transition metal complexes used as catalysts herein can be prepared by several different methods, such as those described by Schwab et al. (1996) *J. Am. Chem. Soc.* 118:100–110, Scholl et al. (1999) *Org. Lett.* 6:953–956, Sanford et al. (2001) *J. Am. Chem. Soc.* 123:749–750, U.S. Pat. No. 5,312,940 and U.S. Pat. No. 5,342,909. Also see U.S. patent application Ser. No. 10/115,581 to Grubbs, Morgan, Benitez, and Louie, filed Apr. 2, 2002, for "One-Pot Synthesis of Group 8 Transition Metal Carbene Complexes Useful as Olefin Metathesis Catalysts," commonly assigned herewith to the California Institute of Technology.

The transition metal complexes used as catalysts herein, particularly the ruthenium carbene complexes, have a well-defined ligand environment that enables flexibility in modifying and fine-tuning the activity level, stability, solubility and ease of recovery of these catalysts. See, e.g., U.S. Pat. No. 5,849,851 to Grubbs et al. In addition, the solubility of the carbene complexes may be controlled by proper selection of either hydrophobic or hydrophilic ligands, as is well known in the art. The desired solubility of the catalyst will largely be determined by the solubility of the reaction substrates and reaction products. It is well known in the art to design catalysts whose solubility is distinguishable from that of the reaction substrates and products, thereby facilitating recovery of the catalyst from the reaction mixture.

III. Synthesis of Macrocycles by Ring Expansion Metathesis (REM):

In another embodiment, a more dilute reaction (about 50 to 150 times less than requested for ROMP) of the monomers that are described below yields a ring expansion process for making macrocycles. The invention provides a method for synthesizing a macrocycle by ring expansion of a cyclic olefin, comprising three metathesis steps in the following order:

(i) a ring-opening metathesis (ROM) reaction step of the cyclic olefin;

(ii) a cross metathesis (CM) step reaction with a diene having two terminal olefinic groups; and (iii) a ring closure metathesis (RCM) reaction step;

wherein steps (i)–(iii) are carried out in the present of a catalytically effective amount of an olefin metathesis catalyst under reaction conditions effective to allow each of the three metathesis reactions to occur.

A preferred such process is wherein the reaction conditions of step (ii) or (iii) comprise carrying out the metathesis in the presence of a catalytically effective amount of the olefin metathesis catalyst of step (i). Further preferred is such a process wherein the reactions conditions of steps (ii) and (iii) comprise carrying out the CM and RCM metathesis in the presence of a catalytically effective amount of the olefin metathesis catalyst of step (i). The intermediates may not be isolated during the process or may optionally be isolated between either step (i) and step (ii) or between step (ii) and step (iii), or between both steps. In a preferred process, following step (iii) the macrocycle is isolated and purified following step (iii), and may optionally be further modified before or after isolation. Preferred further modification of the macrocycle may comprise removing protecting groups, hydrogenating olefinic bonds, hydrogenating carbonyl groups, substituting a second cyclic olefin residue into the alternating copolymer by a cross metathesis insertion to replace olefinic residues from the polyolefin intermediate, combinations thereof, and the like.

In one embodiment, the diene having two terminal olefinic groups is generated in situ from a cyclic diene via a ring-opening cross metathesis (ROCM) reaction.

In a preferred process, the diene having two terminal olefinic groups is present in the reaction solution in a molar concentration range from 0.003 to 0.010, more preferably in a range from 0.005 to 0.007. A preferred such process is wherein the metathesis catalyst is present in a range from 0.01 to 0.20 molar equivalents with respect to the diene, more preferably in a range from in 0.02 to 0. 10, even more preferably in a range from 0.04 to 0.06, and most preferably in about 0.05 molar equivalents with respect to the diene.

The ring expansion metathesis process may be carried out in any metathesis solvent system, preferably in an organic solvent. Preferred organic solvents for the process are toluene, dichloromethane, dichloroethane, and the like.

In a preferred ring expansion process the cyclic olefin is present in a ratio of from 1:1 to 25:1 with respect to the diene, preferably from 1:1 to 5:1, more preferably from 1.1:1 to 2:1, and most preferably at about 1:1:1.

As an example, the cyclic olefin monomer has the structure of formula (IV)

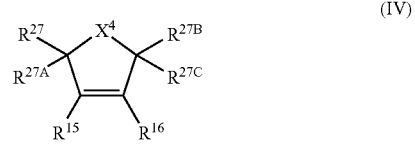

wherein the various substituents are as follows:

$X^4$ is a one-atom to five-atom linkage. In a preferred embodiment, and when the monomer is bicyclic (e.g., when $R^{27}$ and $R^{27B}$ are linked), then X is a one-atom or two-atom linkage, i.e., a linkage that introduces one or two optionally substituted spacer atoms between the two carbon atoms to which $X^4$ is bound. Generally, although not necessarily, $X^4$ will be of the formula —$CR^{19}R^{20}$—$(X^5)_h$— wherein h is zero or 1, $X^5$ is $CR^{21}R^{22}$, O, S, or $NR^{23}$, and $R^{19}$, $R^{20}$, $R^{21}$, $R^{22}$, and $R^{23}$ are independently selected from hydrogen, hydrocarbyl (e.g., $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, $C_6$–$C_{24}$ aralkyl, $C_1$–$C_{20}$ alkyl, $C_5$–$C_{20}$ aryl, $C_5$–$C_{30}$ aralkyl, or $C_5$–$C_{30}$ alkaryl), substituted hydrocarbyl (e.g., substituted $C_1$–$C_{20}$ alkyl, $C_2$–$C_{20}$ alkenyl, $C_2$–$C_{20}$ alkynyl, $C_5$–$C_{20}$ aryl, $C_6$–$C_{24}$ alkaryl, $C_6$–$C_{24}$ aralkyl, $C_1$–$C_{20}$ alkyl, $C_5$–$C_{20}$ aryl, $C_5$–$C_{30}$ aralkyl, or $C_5$–$C_{30}$ alkaryl), heteroatom-containing hydrocarbyl (e.g., $C_1$–$C_{20}$ heteroalkyl, $C_5$–$C_{20}$ heteroaryl, heteroatom-containing $C_5$–$C_{30}$ aralkyl, or heteroatom-containing $C_5$–$C_{30}$ alkaryl), substituted heteroatom-containing hydrocarbyl (e.g., substituted $C_1$–$C_{20}$ heteroalkyl, $C_5$–$C_{20}$ heteroaryl, heteroatom-containing $C_5$–$C_{30}$ aralkyl, or heteroatom-containing $C_5$–$C_{30}$ alkaryl) and protected and unprotected functional groups such as those enumerated in part (I) of this section. Protected functional groups include, by way of example, protected hydroxyl groups, wherein the protecting group is t-butyl silyl (TBS), acyl, or tetrahydropyranyl.

When h is 1, preferred linkages are wherein $X^5$ is $CR^{21}R^{22}$, giving rise to a substituted or unsubstituted ethylene moiety. That is, when $R^{19}$, $R^{20}$, $R^{21}$, and $R^{22}$ are hydrogen, then $X^4$ is ethylene. When h is zero, the linkage is substituted or unsubstituted methylene, and a particularly preferred linkage within this group is methylene per se (i.e., when $R^{19}$ and $R^{20}$ are both hydrogen.)

One of $R^{15}$ and $R^{16}$ is hydrogen and the other is selected from hydrogen, hydrocarbyl (e.g., $C_1$–$C_{20}$ alkyl, $C_5$–$C_{20}$ aryl, $C_5$–$C_{30}$ aralkyl, or $C_5$–$C_{30}$ alkaryl), substituted hydrocarbyl (e.g., substituted $C_1$–$C_{20}$ alkyl, $C_5$–$C_{20}$ aryl, $C_5$–$C_{30}$ aralkyl, or $C_5$–$C_{30}$ alkaryl), heteroatom-containing hydrocarbyl (e.g., $C_1$–$C_{20}$ heteroalkyl, $C_5$–$C_{20}$ heteroaryl, heteroatom-containing $C_5$–$C_{30}$ aralkyl, or heteroatom-containing $C_5$–$C_{30}$ alkaryl), substituted heteroatom-containing hydrocarbyl (e.g., substituted $C_1$–$C_{20}$ heteroalkyl, $C_5$–$C_{20}$ heteroaryl, heteroatom-containing $C_5$–$C_{30}$ aralkyl, or heteroatom-containing $C_5$–$C_{30}$ alkaryl), and -(L)$_v$-Fn wherein v is zero or 1, L is hydrocarbylene, substituted hydrocarbylene and/or heteroatom-containing hydrocarbylene, and Fn is a protected or unprotected functional group. Preferred functional groups include, without limitation, hydroxyl, sulfhydryl, $C_1$–$C_{20}$ alkoxy, $C_5$–$C_{20}$ aryloxy, $C_2$–$C_{20}$ acyloxy, $C_2$–$C_{20}$ alkoxycarbonyl, $C_6$–$C_{20}$ aryloxycarbonyl, halocarbonyl, carboxy, carbamoyl, mono-($C_1$–$C_{20}$ alkyl)-substituted carbamoyl, di-($C_1$–$C_{20}$ alkyl)-substituted carbamoyl, mono-($C_5$–$C_{20}$ aryl)-substituted carbamoyl, cyano, cyanato, formyl, amino, mono- and di-substituted amino, nitro, nitroso, sulfo, $C_1$–$C_{20}$ alkylsulfanyl, $C_5$–$C_{20}$ arylsulfanyl, $C_1$–$C_{20}$ alkylsulfonyl, $C_5$–$C_{20}$ arylsulfonyl, $C_1$–$C_{20}$ alkylsulfinyl, $C_5$–$C_{20}$ arylsulfinyl, boryl, borono, boronato, phospho, phosphino, silyl, and silyloxy. Most preferably, $R^{15}$ and $R^{16}$ are hydrogen.

$R^{27}$, $R^{27A}$, $R^{27B}$, and $R^{27C}$ are independently selected from hydrogen, hydrocarbyl (e.g., $C_1$–$C_{20}$ alkyl, $C_5$–$C_{20}$ aryl, $C_5$–$C_{30}$ aralkyl, or $C_5$–$C_{30}$ alkaryl), substituted hydrocarbyl (e.g., substituted $C_1$–$C_{20}$ alkyl, $C_5$–$C_{20}$ aryl, $C_5$–$C_{30}$ aralkyl, or $C_5$–$C_{30}$ alkaryl), heteroatom-containing hydrocarbyl (e.g., $C_1$–$C_{20}$ heteroalkyl, $C_5$–$C_{20}$ heteroaryl, heteroatom-containing $C_5$–$C_{30}$ aralkyl, or heteroatom-containing $C_5$–$C_{30}$ alkaryl), substituted heteroatom-containing hydrocarbyl (e.g., substituted $C_1$–$C_{20}$ heteroalkyl, $C_5$–$C_{20}$ heteroaryl, heteroatom-containing $C_5$–$C_{30}$ aralkyl, or heteroatom-containing $C_5$–$C_{30}$ alkaryl), and -(L)$_v$-Fn wherein v, L and Fn are defined above. Additionally, any two or more of $R^{27}$, $R^{27A}$, $R^{27B}$, and $R^{27C}$ can be taken together to form a cyclic group, which may be, for example, five- or six-membered rings, or two or three five- or six-membered rings, which may be either fused or linked. The cyclic groups may be aliphatic or aromatic, and may be heteroatom-containing and/or substituted.

One group of such cyclic olefins are those of formula (IV) wherein $R^{27A}$ and $R^{27C}$ are hydrogen, $R^{27}$ is -(L)$_v$-Fn wherein v is zero and -Fn is —$X^{3A}$—($R^{18}$)$_n$, and $R^{27B}$ is -(L)$_v$-Fn wherein v is zero and -Fn is —$X^3$—($R^{17}$)$_m$, and further wherein $X^3$ and $X^{3A}$ are directly or indirectly linked. In this embodiment, then, the cyclic olefin monomer has the structure of formula (VII)

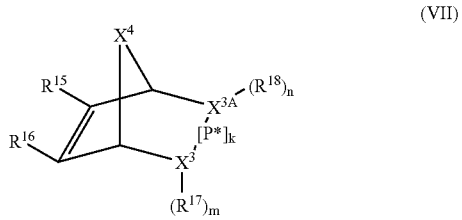

(VII)

in which:

$X^4$, $R^{15}$, and $R^{16}$ are as defined above with respect to olefin monomers of formula (IV);

$X^3$ and $X^{3A}$ are independently N, O, or S;

k is zero or 1;

m and n are independently zero or 1;

P* is a heteroatom-protecting group;

$R^{17}$ and $R^{18}$ are independently selected from hydrogen, hydrocarbyl, substituted hydrocarbyl, heteroatom-containing hydrocarbyl, substituted heteroatom-containing hydrocarbyl, and amino protecting groups, wherein $R^{17}$ and $R^{18}$ may be taken together to form a cyclic group., with the provisos that:

when $X^3$ is O or S, then m is zero;

when $X^{3A}$ is O or S, then n is zero;

when $X^3$ is N, then m is 1; and when $X^{3A}$ is N, then n is 1.

Preferred olefin monomers having the structure of formula (VII) are those wherein the various substituents are as follows:

P* is a protecting group, particularly a heteroatom-protecting group. P* must be inert with respect to the reagents and reaction conditions used for polymerization as well as the reagents and conditions used for any subsequent reactions (e.g., hydrogenation, as described infra), but must be removable following completion of ROMP and any subsequent polymer modification reactions. As may be deduced from the structure of formula (VII) and the above definitions, P* is a protecting group for functional groups having the structure —$X^3$H (or —$X^{3A}$H), wherein $X^3$ (or $X^{3A}$) is O or S. Accordingly, when $X^3$ and $X^{3A}$ are O or S, P* will be a protecting group "linkage" used to protect 1,3-diols and 1,3-dithiols, respectively. A number of such bifunctional protecting groups are known in the art and described, for example, in Greene et al., *Protective Groups in Organic Synthesis*, 3$^{rd}$ Ed. (New York: Wiley, 1999). In the present method, a preferred protecting group for 1,3-diols (i.e., cyclic olefins of formula (VII) wherein $X^3$ and $X^{3A}$ is OH) is —Si($R^{24}$)$_2$— wherein $R^{24}$ is tertiary alkyl, preferably tertiary lower alkyl, e.g., t-butyl, and the deprotecting agent normally used is tetrabutylammonium fluoride. Other preferred protecting groups for 1,3-diols are cyclic acetals and ketals, such as methylene acetal, ethylidene acetal, t-butylmethylidene ketal, 1-t-butylethylidene ketal, 1-phenylethylidene ketal, cyclopentylidene ketal, cyclohexylidene ketal, benzylidene acetal, and acetonide (isopropylidene ketal), with acetonide particularly preferred. Such groups are typically removed via acid hydrolysis, preferably, although not necessarily, at an elevated temperature. With acetonide-protected 1,3-diols, deprotection may be achieved not only via acid hydrolysis, but also using other means, e.g., with boron trichloride or bromine. Preferred protecting groups for 1,3-dithiols (i.e., cyclic olefins of formula (VII) wherein $X^3$ is SH) are methylene, benzylidene (both removable with sodium/ammonia), and isopropylidene (removable with mercury (II) chloride).

$R^{17}$ and $R^{18}$ are independently selected from hydrogen, hydrocarbyl, substituted hydrocarbyl, heteroatom-containing hydrocarbyl, substituted heteroatom-containing hydrocarbyl, and amino protecting groups. $R^{17}$ and $R^{18}$ may also be linked to form a protecting group linking the nitrogen atoms to which they are attached. Removal of such protecting groups and regeneration of the unprotected amino moieties can be carried out using the method of Bøgevig et al. (2002) *Angew. Chem. Int. Ed.* 41:1790–1793.

Representative olefin monomers of formula (VII) in which $X^3$ and $X^{3A}$ are different are those wherein k and m are zero, n is 1, $X^3$ is O, $X^{3A}$ is N, and $R^{18}$ is an amino protecting group, e.g., a carboxylic acid ester such as —(CO)—O-t-Bu. When $X^4$ is methylene, and $R^{15}$ and $R^{16}$ are hydrogen, the monomer is 2-oxa-3-aza-bicyclo[2.2.1]hept-5-ene-3-carboxylic acid t-butyl ester, having the structure (VIIB)

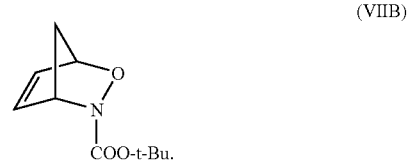

(VIIB)

The monomer can be readily synthesized using a hetero-Diels Alder reaction. See Mulvihill et al. (1998), *J. Org. Chem.* 63:3357. Following polymerization, deprotection can be achieved using the method of Vogt et al. (1998) *Tetrahedron* 54:1317–1348.

Representative olefin monomers of formula (VII) in which $X^3$ and $X^{3A}$ are the same are those wherein $X^3$ and $X^{3A}$ are O, k is 1, m, and n are zero, and P* is a protecting group for 1,3-diols. When $X^4$ is methylene, and $R^{15}$ and $R^{16}$ are hydrogen, an exemplary monomer is 3,3-di-tert-butyl-2,4-dioxa-3-sila-bicyclo[3.2.1]oct-6-ene (olefin compound (3) hereinafter).

As another example of useful cyclic olefin monomers, $R^{27A}$ and $R^{27C}$ of formula (IV) are hydrogen, in which case the cyclic olefin has the structure of formula (VIIa)

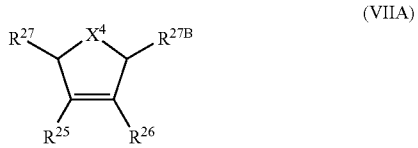

(VIIA)

wherein $X^4$, $R^{27}$, and $R^{27B}$ are as defined previously, and $R^{25}$ and $R^{26}$ are defined as for $R^{15}$ and $R^6$.

Exemplary monocyclic olefins encompassed by formula (VIIA) (i.e., olefins wherein $R^{27}$ and $R^{27B}$ are not linked) include, without limitation, cyclopentene, 3-methylcyclopentene, 4-methylcyclopentene, 3-t-butyldimethyl silyloxycyclopentene, 4-t-butyl-dimethylsilyloxycyclopentene, cyclohexene, 3-methylcyclohexene, 4-methyl-cyclohexene, 3-t-butyldimethylsilyloxycyclohexene, 4-t-butyldimethylsilyloxycyclohexene, cycloheptene, 3-methylcycloheptene, 4-methylcycloheptene, 5-methylcycloheptene, 3-t-butyldimethylsilyloxycycloheptene, 4-t-butyldimethylsilyloxycycloheptene, 5-t-butyldimethylsilyloxycycloheptene, cyclooctene, 3-methylcyclooctene, 4-methylcyclooctene, 5-methylcyclooctene, 3-t-butyldimethyl-silyloxycyclooctene, 4-t-butyldimethylsilyloxycyclooctene, 5-t-butyldimethylsilyloxycyclooctene, cyclononene, 3-methylcyclononene, 4-methylcyclononene, 5-methylcyclononene, 6-methylcyclo-nonene, 3-t-butyldimethylsilyloxycyclononene, 4-t-butyldiinethylsilyloxycyclononene, 5-t-butyl-dimethylsilyloxycyclononene, 6-t-butyldimethylsilyloxycyclononene, cyclodecene, 3-methylcyclo-decene, 4-methylcyclodecene, 5-methylcyclodecene, 6-methylcyclodecene, 3-t-butyldimethylsilyloxycyclodecene, 4-t-butyldimethylsilyloxycyclononene, 5-t-butyldimethylsilyloxycyclodecene, 6-t-butyldimethylsilyloxycyclodecene, cycloundecene, 3-methylcycloundecene, 4-methylcycloundecene, 5-methylcycloundecene, 6-methylcycloundecene, 7-methylcycloundecene, 3-t-butyl-dimethylsilyloxycycloundecene, 4-t-butyldimethylsilyloxycycloundecene, 5-t-butyldimethylsilyloxy-cycloundecene, 6-t-butyldimethylsilyloxycycloundecene, 7-t-butyldimethylsilyloxycycloundecene, cyclododecene, 3-methylcyclododecene, 4-methylcyclododecene, 5-methylcyclododecene, 6-methyl-cyclododecene, 7-methylcyclododecene, 3-t-butyldimethylsilyloxycyclododecene, 4-t-butyldimethylsilyloxycyclododecene, 5-t-butyldimethylsilyloxycyclododecene, 6-t-butyldimethylsilyloxycyclododecene, and 7-t-butyldimethylsilyloxycyclododecene.

More preferred cyclic olefins are members selected from the group cyclopentene, 3-methylcyclopentene, 3-t-butyldimethylsilyloxycyclopentene, cyclohexene, 4-methylcyclohexene, 4-t-butyldimethylsilyloxycyclohexene, cycloheptene, cyclooctene, 5-methylcyclooctene, 5-t-butyldimethylsilyloxycyclooctene, cyclononene, and cyclododecene.

The olefin expansion reaction is generally carried out in an inert atmosphere by dissolving a catalytically effective amount of an olefin metathesis catalyst (preferably a Group 8 transition metal complex of formula (I)) in a solvent, and adding the bicyclic or polycyclic olefin monomer (preferably a monomer of formula (VII)), optionally dissolved in a solvent, to the catalyst solution. Preferably, the reaction is agitated (e.g., stirred). The progress of the reaction can be monitored by standard techniques, e.g., nuclear magnetic resonance spectroscopy. Examples of solvents that may be used in the olefin expansion reaction include organic, protic, or aqueous solvents that are inert under the polymerization conditions, such as aromatic hydrocarbons, chlorinated hydrocarbons, ethers, aliphatic hydrocarbons, alcohols, water, or mixtures thereof. Preferred solvents include benzene, toluene, p-xylene, methylene chloride, 1,2-dichloroethane, dichlorobenzene, chlorobenzene, tetrahydrofuran, diethylether, pentane, methanol, ethanol, water, or mixtures thereof. More preferably, the solvent is benzene, toluene, p-xylene, methylene chloride, 1,2-dichloroethane, dichlorobenzene, chlorobenzene, tetrahydrofuran, diethylether, pentane, methanol, or ethanol. Most preferably, the solvent is toluene or 1,2-dichloroethane. The solubility of the macrocycle formed in the olefin ring expansion reaction will depend on the choice of solvent and the molecular weight of the acrocycle obtained. Under certain circumstances, no solvent is needed.

Reaction temperatures can range from about 0° C. to 100° C., and are preferably in the range of about 25° C. to 75° C., and the reaction time will generally be in the range of about 12 to 48 hours. The molar ratio of cyclic olefin monomer to the catalyst is selected based on the desired macrocycle, and the activity of the particular catalyst. As the present method is a controlled ring expansion, there is a relationship between the activity of the cyclic olefin and the ring expansion (see Examples and Tables below). With more active catalysts, the cyclicolefin/catalyst ratio can proceed with far less catalyst, so that the [monomer]/[catalyst] ratio can be extraordinarily high (see Example 2), reducing overall cost significantly. In general, the transition metal carbene complexes of formula (IIA) are more active than the bisphosphine catalysts of formula (I) (i.e., complexes wherein $L^1$ and $L^2$ are tri-substituted phosphines or analogous ligands, as explained in part (II)).

In order to provide a saturated ring-expanded olefin macrocycle, the unsaturated macrocycle produced is hydrogenated using conventional reagents and conditions, e.g., using tosyl hydrazide, hydrogenation under pressure with a hydrogenation catalyst and the like. The resulting hydrogenated macrocycles are described in greater detail below.

Deprotection of functional groups is then effected, using a reagent effective to provide a deprotected macrocycle.

For most applications, highly functionalized macrocycles are preferred. Thus, it is desirable that the catalyst used to form such macrocycles be stable in the presence of functional groups. The Group 8 transition metal complexes described in part (II) are, in fact, stable with respect to a wide variety of functional groups, as described, for example, in U.S. Pat. Nos. 5,312,940, 5,342,909, 5,917,071 5,969,170, 6,111,121, and 6,313,332 to Grubbs et al., and in U.S. patent application Ser. No. 10/114,418 to Grubbs et al., filed Apr. 1, 2002, for "Cross-Metathesis Reaction of Functionalized and Substituted Olefins Using Group 8 Transition Metal Carbene Complexes as Metathesis Catalysts," all of which are commonly assigned herewith to the California Institute of Technology.

In one embodiment the invention provides such a metathesis process wherein the catalysis is a Group 8 transition metal complex as described above. In a preferred process t he metathesis catalyst is present in 0.0005 to 0.05 molar equivalents with respect to the cyclic olefin. Preferably, the diene is present in the reaction solution (such as an organic solvent) in a molar concentration from 0.001 to 0.01, more preferably 0.002 to 0.007, and most preferably from 0.003 to 0.006 or about 0.005. Preferably, the cyclic olefin monomer is present in a molar ratio from 1:1 to 25:1 with respect to the diene, more preferably 1:1 to 5:1, even more preferably from 1:1 to 2:1 and most preferably about 1.1:1. Preferably the metathesis catalyst is present in about 5 moles percent with respect to the cyclic olefin when the cyclic olefin is present in a ratio of 1.1:1 to 2:1 with respect to the diene.

A. Dienes with two Terminal Olefinic Groups for the REM Invention

Preferred dienes having two terminal olefinic groups that are useful in REM as would be useful for an alternating copolymer ROIMP process. Only the concentration needs to be varied to provide a more dilute molar concentration, as described above.

Preferred dienes having two terminal olefinic groups that are useful in the methods according to the invention are dienes wherein are the two terminal olefinic groups of the diene are joined by a hydrocarbylene linker group comprising 6–30 carbon atoms and the carbon atoms of the linker group may be substituted or unsubstituted and the linker group may be interrupted by up to 6 hetero atoms selected from O, S and N, and on the linker chain two or more substituents may be linked to form an additional cyclic group. More preferred are such dienes wherein the two terminal olefinic groups of the diene taken together with adjacent atoms of the linker group form a bis-acrylate acyclic diene compound, a bis-vinyl ketone acyclic diene compound, or a bis-allylic acetate acyclic diene compound. Further preferred are such dienes wherein the linker group is hydrocarbylene, substituted hydrocarbylene, heteroatom-containing hydrocarbylene, or substituted heteroatom-containing hydrocarbylene linker, and two or more substituents on adjacent atoms of the chain may be linked to form an additional cyclic group, and wherein up to 6 carbon atoms of the linker group may be substituted by functional groups, or protected functional groups. Preferred functional groups or protected functional groups substituted on the carbon atoms of the linker group are independently selected from halogen, alcohol, oxo, thiol, —SO$_3$—H, a substituted —SO$_2$— group, amino, substituted amino, or combinations thereof.

A preferred acyclic diene useful in the present invention is selected from formula (VIIb) and (VIIc) as follows:

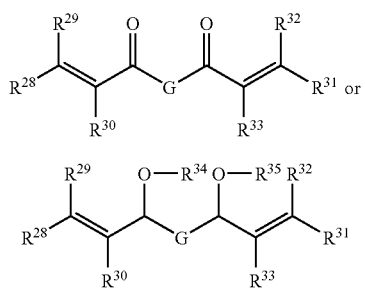

wherein:

$R^{28}$, $R^{29}$, $R^{31}$, and $R^{32}$ are each independently hydrogen or a substituent that does not interfere with olefin cross metathesis;

$R^{30}$ and $R^{33}$ are each independently hydrogen or a leaving group that that does not interfere with olefin cross metathesis;

$R^{34}$ and $R^{35}$ are each independently hydrogen, a non-acyl alcohol protecting group, or an acyl group; and G is hydrocarbylene linker group comprising 6–30 carbon atoms, wherein the carbon atoms of the linker group may be substituted or unsubstituted and the linker group may be interrupted by up to 6 hetero atoms selected from O, S and N, and wherein two or more substituents on the chain may be linked to form an additional cyclic group.

Preferred dienes according to formulae (VIIb) and (VIIc) are such compounds wherein G is a linker chain constructed by 2 to 24 linked —$X^7$— groups, wherein each occurrence of $X^7$ in the linker chain is independently selected from $CR^{36}R^{37}$, O, S, or $NR^{38}$, and $R^{36}$, $R^{37}$, and $R^{38}$ are independently selected from hydrogen, substituted hydrocarbyl, heteroatom-containing hydrocarbyl, substituted heteroatom-containing hydrocarbyl, functional groups and protected functional groups, wherein up to 6 pairs of $CR^{36}R^{37}$ groups of the linker chain may be independently interrupted by an O, S, or $NR^{38}$ group.

A particularly preferred diene is a compound having one of the following structures:

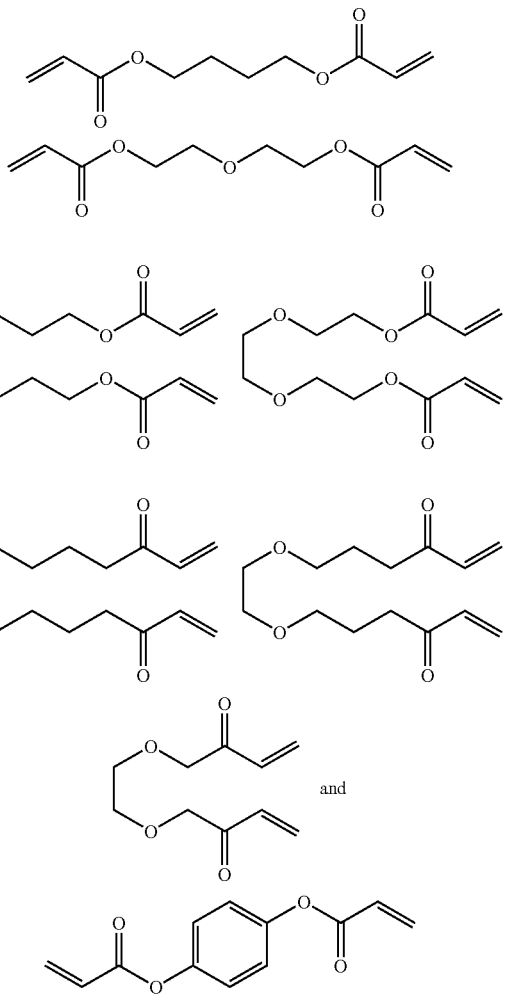

B. Macrocycle Example Structures from the REM Invention

Preferred macrocycles produced by ring expansion according to the invention are as follows:

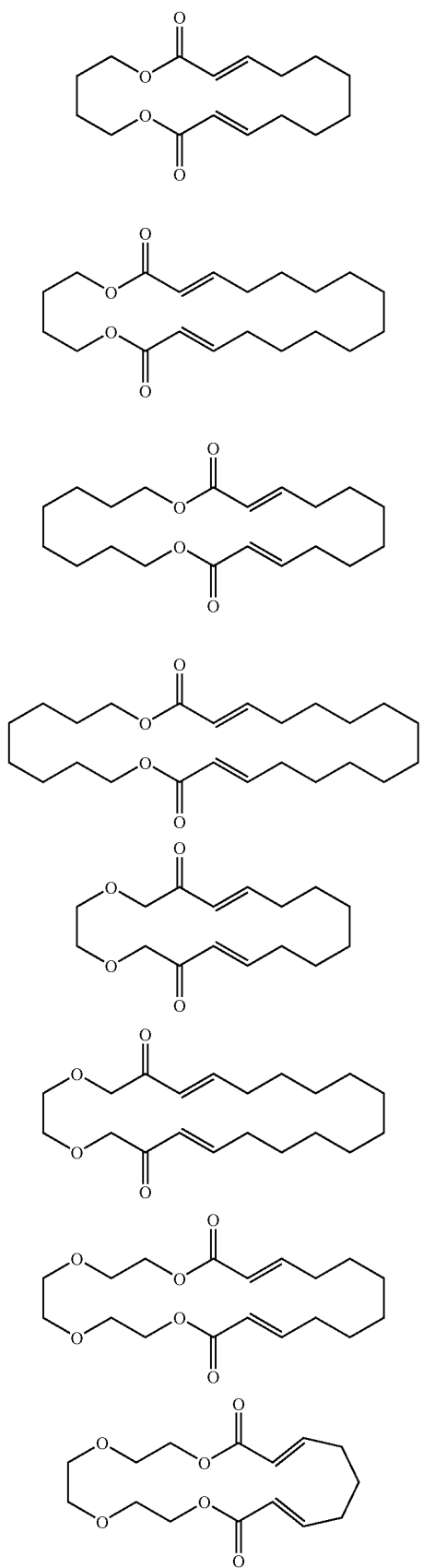
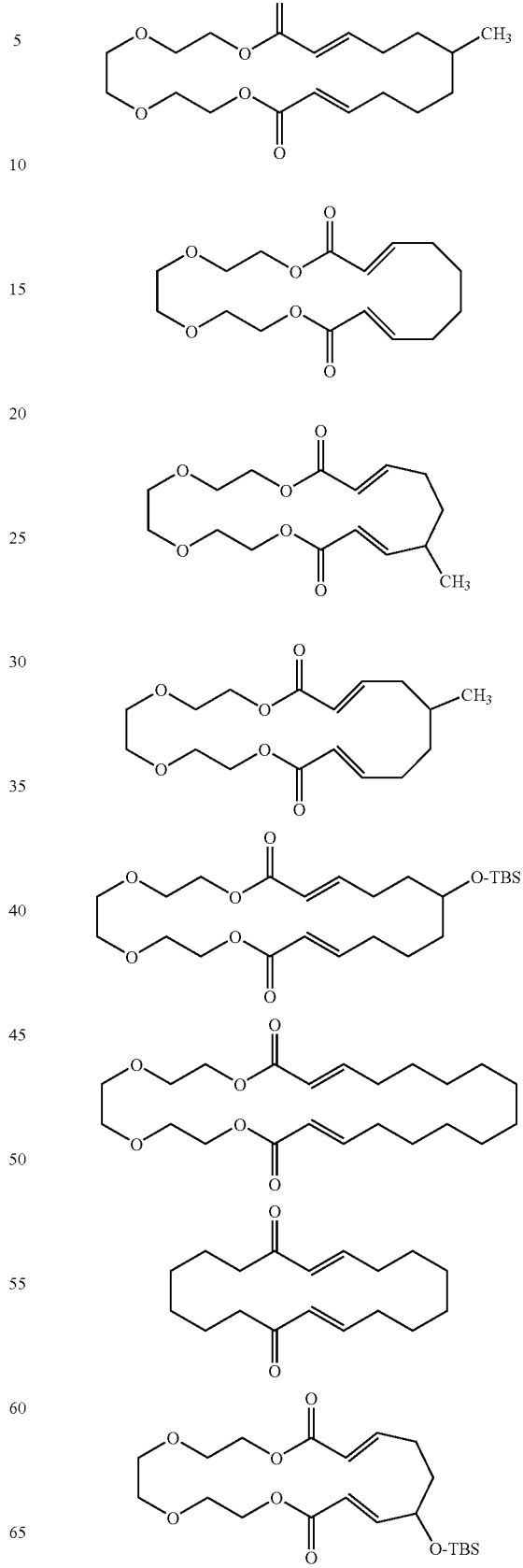

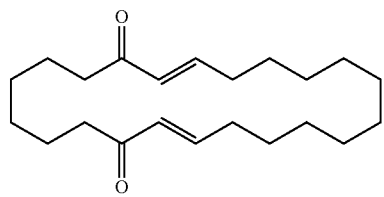
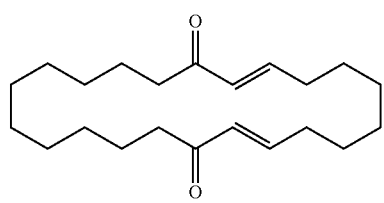
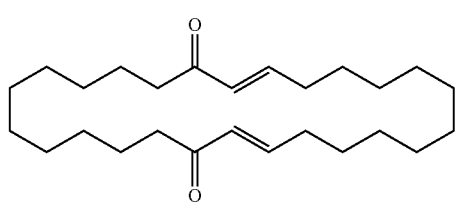
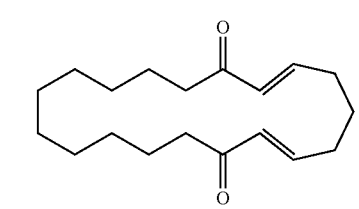
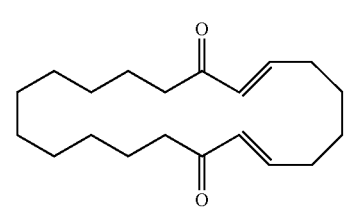
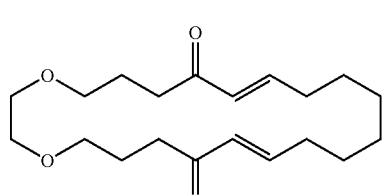
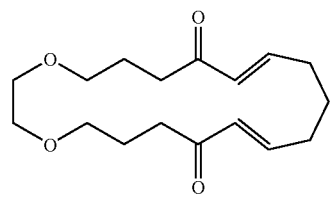
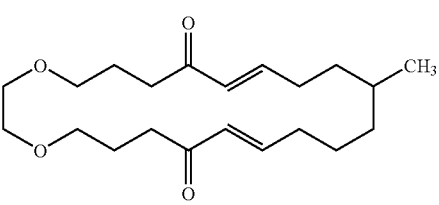
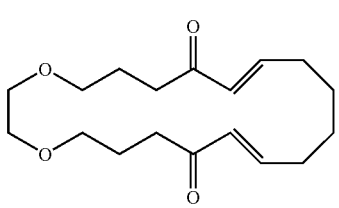
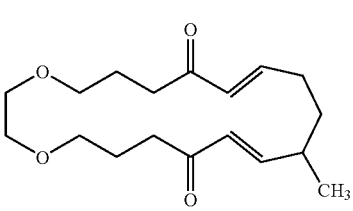
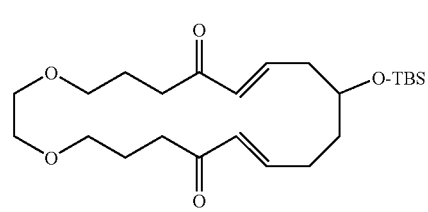
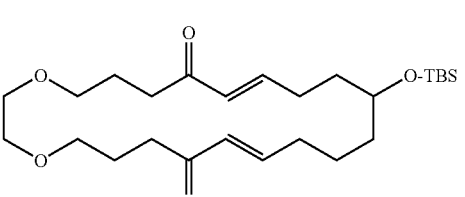
and

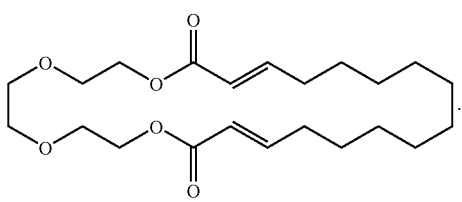

Preferred such macrocycle structures comprise structures obtained from the additional step of removing the TBS alcohol protecting group from the olefin macrocycle. Also preferred are such macrocycles that have undergone a further step of hydrogenating one or more double bonds of the olefin macrocycle. Preferred such hydrogenated macrocycles have structures as follows:

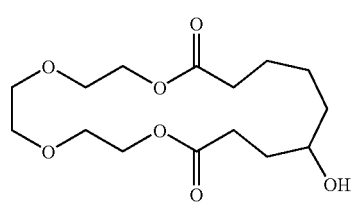

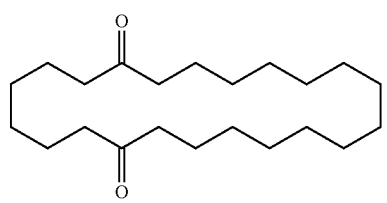

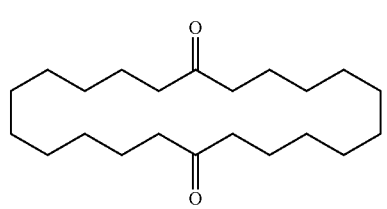

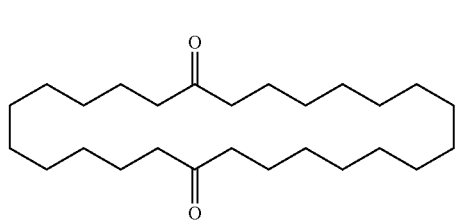

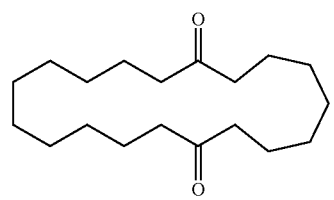

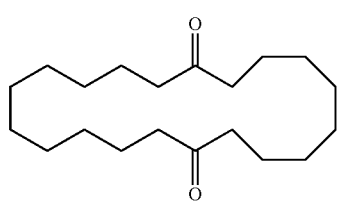

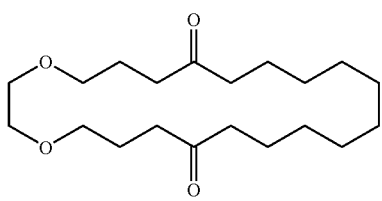

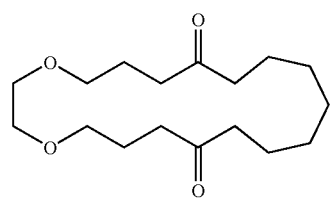

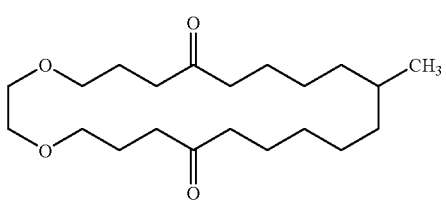

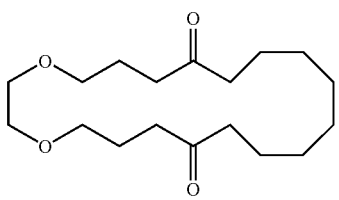

-continued

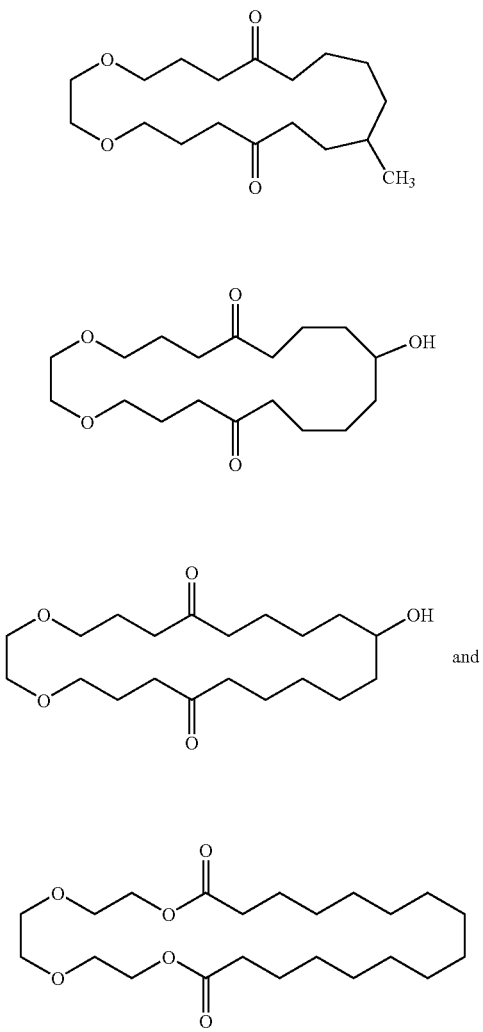

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

EXPERIMENTAL

Ring Expansion via Olefin Metathesis to Produce Macromolecules

General Procedures. NMR spectra were recorded on Varian-300 NMR. Chemical shifts are reported in parts per million (ppm) downfield from tetramethylsilane (TMS) with reference to internal solvent. Multiplicities are abbreviated as follows: singlet (s), doublet (d), triplet (t), quartet (q), quintet (quint), and multiplet (m). The reported $^1$H NMR data refer to the major olefin isomer unless stated otherwise. The reported $^{13}$C NMR data include all peaks observed and no peak assignments were made. High-resolution mass spectra (EI and FAB) were provided by the UCLA Mass Spectrometry Facility (University of California, Los Angeles). Analytical thin-layer chromatography (TLC) was performed using silica gel 60 F254 precoated plates (0.25 mm thickness) with a fluorescent indicator. Flash column chromatography was performed using silica gel 60 (230–400 mesh) from EM Science. All other chemicals were purchased from the Aldrich, Strem, or Nova Biochem Chemical Companies, and used as delivered unless noted otherwise. $CH_2Cl_2$ was purified by passage through a solvent column prior to use. The solvent columns are composed of activated alumina (A-2) and supported copper redox catalyst (Q-5 reactant). See: A. B. Pangborn, M. A. Giardello, R. H. Grubbs, R. K. Rosen, F. J. Timmers, *Organometallics* 1996, 15, 1518–1520.

Materials. If necessary, non-anhydrous solvents were dried by passage through solvent purification columns. Cyclic olefins (>99%) were obtained from as described above unless otherwise stated and were used as received. Acyclic dienes were obtained from as described above and degassed by an argon purge prior to use. N,N-Dimethylformamide (anhydrous) (DMF), Toluene (anhydrous), dichloromethane (anhydrous), 1,2-dichloroethane (anhydrous), 2,6-lutidine (99+%, redistilled), and di-tert-butylsilylbis(trifluoromethanesulfonate) (97%) were obtained from Aldrich and used as received (after optionally being dried). $(PCy_3)_2(Cl)_2Ru=CHPh$ (1) was synthesized according to Schwab et al. (1996) *J. Am. Chem. Soc.* 118:100–110, $(ImesH_2)$—$(PCy_3)(Cl)_2Ru=CHPh$ (2) was synthesized as described in Sanford et al. (2001) *J. Am. Chem. Soc.* 123:749–750, and 3,3-di-tert-butyl-2,4-dioxa-3-sila-bicyclo[3.2.1]oct-6-ene (3) was synthesized according to Lang et al. (1994) *Helv. Chim. Acta* 77:1527–1540.

The general procedures and materials as described above were performed where a low concentration of the two monomers (approximately 100 times more dilute than for polymerization) and proportionally lower amount of the metathesis catalyst are utilized in order to prevent or slow polymerization in favor of ring expansion metathesis. As a general procedure, a flask is charged with catalyst 2 (0.05 equiv of a 0.005 to 0.007 molar solution in $CH_2Cl_2$), and the α,β-unsaturated carbonyl compounds (dienes), and cycloalkenes were added via syringe in a quantity sufficient to create a 0.005 to 0.007 molar solution for each reactant. The flask was fitted with a condenser and refluxed under argon for 12 hours. The progress of the reaction was monitored by TLC. After the solvent was evaporated, the product was purified directly on a silica gel column.

For a successful ring expansion, several conditions must be satisfied. The cycloalkenes must be able to undergo the ring-opening reaction. Once opened, they must react selectively with the acyclic diene for CM and RCM to minimize side products. In addition, the acyclic diene should not undergo reactions with itself such as cyclization or cross metathesis. To illustrate this process bis-acrylates and bis-vinyl ketones systems are utilized, because they are known to react selectively with terminal olefins in excellent yields and less favorably with themselves. This provides an efficient and mild route for the synthesis of macrocycles, especially carbocycles, which is considered harder than macrolactonization or lactamization. This illustrates the novel method of forming macrocycles by a ring expansion reaction in which three types of olefin metathesis (ring-opening, cross, and ring-closing) reactions occur sequentially to yield macrocycles. Process efficiency is improved by the higher activity of catalyst 2; not only in improved yields, but also by reducing the catalyst loading and more importantly, in improved stereoselectivity of the newly formed olefins.

Ring Expansion of Cyclic Olefin and Bis-vinyl Ketone Dienes via Sequential ROM, CM and RCM with Catalyst (2) to form Macrocycles

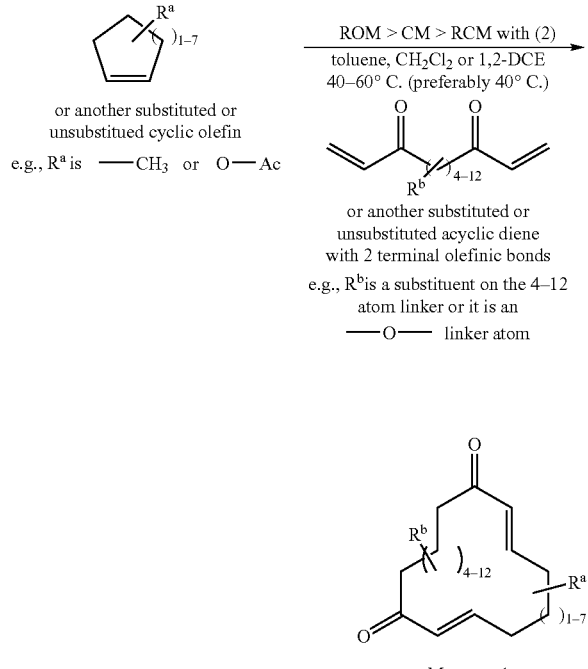

SCHEME 1

EXAMPLE 1

Using the above general macrocyclization procedures, catalyst 2 (5 mol %) was added to a solution of the acyclic diene having two terminal olefinic groups (e.g., bis-vinyl ketone with octylene linker group) and the cyclic olefin (e.g., cyclopentene) (5 equiv) in an organic solvent (e.g., $CH_2Cl_2$) (5 mM of cyclopentene in the acyclic diene solution). After refluxing for 12 h, several products were obtained. The two major products were purified directly on a silica gel column, eluting with 1:4=ethyl acetate:hexane. The major products were the (1+1) fashion (acyclic diene and cycloalkene) ring-expanded product (17 carbon ring atoms macrocycle) 10.0 mg. 43% yield ($R_f$=0.4 in 1:2=EA:Hx, colorless liquid) and the double ring-expanded product (34 carbon ring atoms macrocycle) 8.0 mg 34% yield ($R_f$=0.3 in 1:2=EA:Hx, white solid) in a ratio of 1.3/1 (Table 2, entry 8, below). Data for the 17 ring atoms macrocycle is: $^1$H NMR (300 MHz, $CDCl_3$, ppm): δ 6.80(2H, dt, J=6.9, 15.9 Hz), 6.15(2H, dt, J=1.5, 15.9 Hz), 2.49(4H, t, J= 6.9 Hz), 2.29(4H, dq, J=1.2, 6.9 Hz), 1.70(6H, m), 1.29(12H, m). $^{13}$C NMR (75 MHz, $CDCl_3$, ppm): δ 202.2, 146.8, 131.2, 40.0, 31.4, 28.6, 28.5, 28.3, 26.7, 25.7. HRMS (EI) calcd for $C_{19}H_{30}O_2$, 290.2246, found, 290.2241. Data for the 34 ring atoms macrocycle is: $^1$H NMR (300 MHz, $CDCl_3$, ppm): δ 6.79(4H, dt, J=6.9, 15.9 Hz), 6.10(4H, dt, J=1.5, 15.9 Hz), 2.52(8H, t, J=7.29 Hz), 2.24(8H, q, J=6.6 Hz), 1.67(12H, m), 1.27(24H, m). $^{13}$C NMR (75 MHz, $CDCl_3$, ppm): δ 201.0, 145.2, 131.1, 40.4, 31.9, 29.6, 29.4, 29.3, 26.8, 24.5. HRMS (EI) calcd for $C_{38}H_{60}O_4$, 580.4492, found, 580.4486.

EXAMPLE 2

The procedures in Example 1 was followed while increasing the concentration of the cyclic olefin to 25 mM decreased the product ratio of the 17 atom/34 atom products to 1/2 (Table 2, entry 9).

EXAMPLES 3–5

Since cyclooctene polymerizes by ring-opening metathesis much faster than cyclopentene due to its higher ring strain, the relationship of concentration of cyclooctene and product distribution was explored (Table 1, entries 3 to 5) using the general procedures of Example 1. The product was purified directly on a silica gel column, eluting with 1:9=ethyl acetate:hexane. With 5 equiv of cyclooctene (5 mM, 5:1 ratio with respect to the acyclic diene), ROMP polymerization of cyclooctene is a significant side reaction and 23% of the undesired double inserted macrocycle (the acyclic diene is expanded with two cyclooctene monomer residues) is obtained (Table 1, entry 3). The singly expanded product that was obtained in 23% yield had a $R_f$=0.5 in 1:2=EA:Hx, colorless liquid. The data for this structure was: $^1$H NMR (300 MHz, $CDCl_3$, ppm): δ 6.78(2H, dt, J=7.2, 15.9 Hz), 6.09(2H, dt, J=1.5, 15.9 Hz), 2.49(4H, t, J=6.9 Hz), 2.22(4H, dq, J=1.5, 6.9 Hz), 1.63(4H, m), 1.47(4H, m), 1.24 (16H, m). $^{13}$C NMR (75 MHz, $CDCl_3$, ppm): δ 202.2, 148.0, 131.1, 39.8, 32.3, 29.2, 29.0, 28.8, 28.5, 28.1, 25.8. HRMS (EI) calcd for $C_{30}H_{50}O_2$, 442.3811, found, 442.3806. The double expanded product that was obtained in 23% yield had a $R_f$=0.6 in 1:2=EA:Hx, colorless liquid. The data for this structure was: $^1$H NMR (300 MHz, $CDCl_3$, ppm): δ 6.80(2H, m), 6.07(2H, d, J=15.6 Hz), 5.37(2H, m), 2.51(4H, t, J=6.9 Hz), 2.20(4H, m), 2.00(4H, m), 1.6–1.27(24H, m). $^{13}$C NMR (75 MHz, $CDCl_3$, ppm): δ 201.5, 147.8, 130.8, 130.7, 130.5, 40.0, 32.7, 32.6, 28.1–29.8 (m), 24.7. HRMS (EI) calcd for $C_{22}H_{36}O_2$, 332.2715, found, 332.2712. Decreasing the cyclooctene to 2 equiv. (2:1 ratio) increased the ratio of the desired singly expanded product/double expanded product to 1.2/1 ((Table 1, entry 4), and finally the best yield of 53% for the desired singly expanded product was isolated with 1.1:1 ratio (1.1 equiv.) of cyclooctene (Table 1, entry 5).

EXAMPLE 6

Functionalized cyclooctenes are also viable substrates for ring expansion ((Table 1, entry 6). The above procedures were followed generally and the product was purified directly on a silica gel column, eluting with 1:3=ethyl acetate:hexane. A 43% yield (13.0 mg) of the product was obtained ($R_f$=0.4 in 1:2=EA:Hx, colorless liquid). The data was: $^1$H NMR (300 MHz, $CDCl_3$, ppm): δ 6.78(2H, m), 6.12(2H, d, J=16.2 Hz), 4.87(1H, m), 2.50(4H, m), 2.22(4H, m), 2.06(3H, s), 1.6–1.25(14H, m). $^{13}$C NMR (75 MHz, $CDCl_3$, ppm): δ 201.6, 170.8, 146.8, 146.1, 131.2, 131.1, 72.7, 40.2, 40.1, 33.5, 32.9, 32.0, 29.1, 28.9, 28.8, 28.5, 25.7, 25.6, 24.1, 21.6. HRMS (EI) calcd for $C_{24}H_{38}O_4$, 390.2770, found, 390.2770.

TABLE 1
| Entry | Ring Size[b] (Eq.) | Con. (mM) | Ring Products[c] (% Yield[d]) |
|---|---|---|---|
| 1 | 5 (5.0) | 5 | 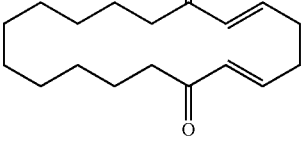 4 (43%)<br>5 (34%) |
| 2 | 5 (5.0) | 25 | 4 (13%):5 (30%) |
| 3 | 8 (5.0) | 5 | 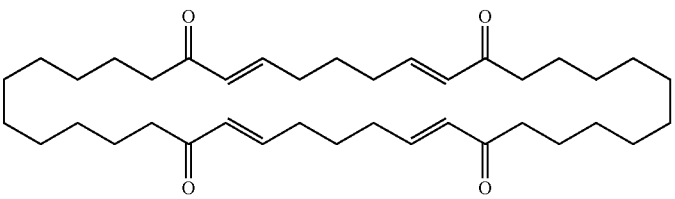 6 (23%)<br>7 (23%) |
| 4 | 8 (2.0) | 5 | 6 (34%):7 (28%) |
| 5 | 8 (1.1) | 5 | 6 (53%) |
| 6 | 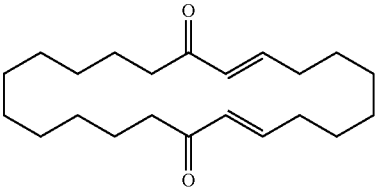 (1.1) | 5 | 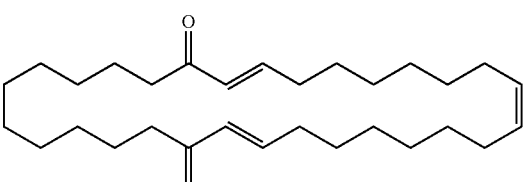 8 (43) |
[a]Reactions were performed in refluxing CH$_2$Cl$_2$ under an atmosphere of argon.
[b]Ring size: 5 (cyclopentene), (8), cyclooctene.
[c]Only (E)-isomers were observed by $^1$H NMR.
[d]Isolated yields. No starting material remained.

Without being bound to any particular mechanism, ring expansion products (as illustrated above) are believed to be obtained in accordance with steps shown below in Scheme 4.

SCHEME 2

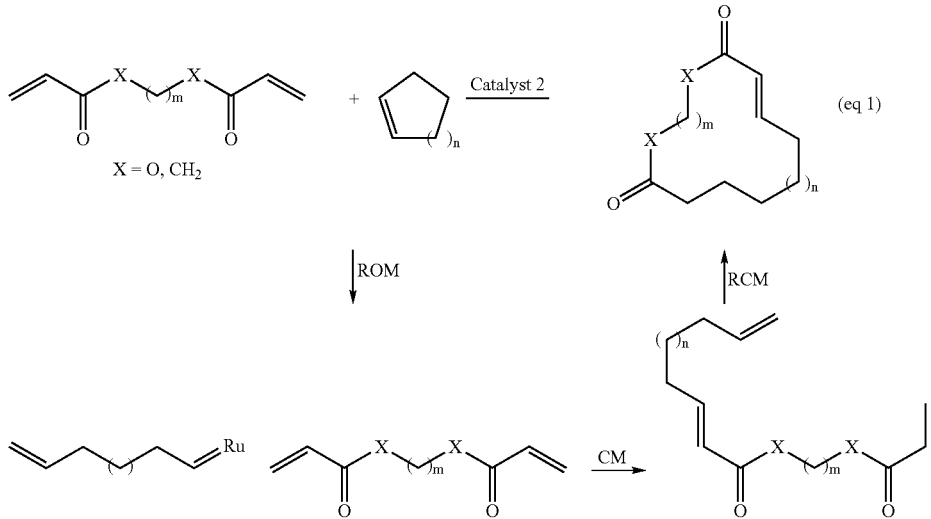

Ring Expansion of Cyclic Olefin and Bis-Acrylate Dienes via Sequential ROM, CM and RCM with Catalyst (2) to form Macrocycles Bis-acrylate dienes may also be expanded in substantially the same manner as for Bis-vinyl ketones. See the following Examples 7–21.

EXAMPLE 7

The procedures of Examples 1–6 were followed. The product was purified directly on a silica gel column, eluting with 1:10=ethyl acetate:hexane. 13.3 mg of the product in 45% yield was obtained ($R_f$=0.3 in 1:5=EA:Hx, colorless liquid). $^1$H NMR (300 MHz, CDCl$_3$, ppm): δ 6.86(2H, dt, J=6.9, 15.6 Hz), 5.73(2H, dt, J=1.5, 15.6 Hz), 4.21(4H, m), 2.20(4H, m), 1.81(4H, m), 1.50(4H, m), 1.23(4H, m). $^{13}$C NMR (75 MHz, CDCl$_3$, ppm): δ 166.7, 149.8, 121.9, 64.0, 31.1, 27.7, 27.1, 26.3. HRMS (EI) calcd for C$_{16}$H$_{24}$O$_4$ 280.1675, found 280.1680.

EXAMPLE 8

The procedures in Example 7 were followed. The product was purified directly on a silica gel column, eluting with 1:10=ethyl acetate:hexane. 18.0 mg of the product was obtained in 45% yield ($R_f$=0.45 in 1:10=EA:Hx, colorless liquid). $^1$H NMR (300 MHz, CDCl$_3$, ppm): δ 6.89(2H, dt, J=6.9, 15.6 Hz), 5.75(2H, d, J=15.6 Hz), 4.15(4H, m), 2.21(4H, m), 1.7(4H, m), 1.45(4H, m), 1.24(12H, m). $^{13}$C NMR (75 MHz, CDCl$_3$, ppm): δ 166.6, 149.7, 122.0, 63.8, 32.3, 29.2, 28.7, 28.1, 27.9, 25.9. HRMS (EI) calcd for C$_{20}$H$_{32}$O$_4$ 336.2301, found 336.2308.

EXAMPLE 9

The procedures in Example 7 were followed. The product was purified directly on a silica gel column, eluting with 1:15=ethyl acetate:hexane. 25.7 mg of the product was obtained in 47% yield ($R_f$=0.4 in 1:10=EA:Hx, colorless liquid). $^1$H NMR (300 MHz, CDCl$_3$, ppm): δ 6.93(2H, dt, J=6.9, 15.6 Hz), 5.82(2H, dt, J=1.8, 15.6 Hz), 4.14(4H, t, J=5.7 Hz), 2.20(4H, m), 1.63(4H, m), 1.5–1.3 (16H, m). $^{13}$C NMR (75 MHz, CDCl$_3$, ppm): δ 166.9, 149.2, 121.7, 64.9, 31.4, 29.5, 29.0, 27.5, 27.1, 26.6. HRMS (EI) calcd for C$_{20}$H$_{32}$O$_4$ 336.2301, found 336.2298.

EXAMPLE 10

The procedures in Example 7 were followed. The product was purified directly on a silica gel column, eluting with 1:15=ethyl acetate:hexane. 28.2 mg of the product was isolated in 42% yield. ($R_f$=0.4 in 1:10=EA:Hx, colorless liquid). $^1$H NMR (300 MHz, CDCl$_3$, ppm): δ 6.92(2H, dt, J=6.9, 15.6 Hz), 5.82(2H, dt, J=1.2, 15.6 Hz), 4.11(4H, t, J=5.7 Hz), 2.20 (4H, m), 1.60 (4H, m), 1.5–1.2 (24H, m). $^{13}$C NMR (75 MHz, CDCl$_3$, ppm): δ 167.0, 149.6, 121.7, 64.5, 32.3, 29.4, 29.3, 29.1, 29.0, 28.5, 28.0, 26.2. HRMS (EI) calcd for C$_{24}$H$_{40}$O$_4$ 392.2927, found 392.2920.

EXAMPLE 11

The procedures in Example 7 were followed. The product was purified directly on a silica gel column, eluting with 1:1=ethyl acetate:hexane. 9.0 mg of the product was obtained in 52% yield ($R_f$=0.3 in 1:1=EA:Hx, white solid). $^1$H NMR (300 MHz, CDCl$_3$, ppm): δ 6.85(2H, dt, J=7.2, 15.6 Hz), 5.84(2H, dt, J=1.5, 15.6 Hz), 4.26(4H, m), 3.72 (4H, m), 3.67(4H, s), 2.29(4H, m), 1.77(2H, m). $^{13}$C NMR (75 MHz, CDCl$_3$, ppm): δ 166.4, 148.1, 123.2, 70.7, 69.3, 63.9, 31.7, 24.6. HRMS (EI) calcd for C$_{15}$H$_{22}$O$_6$ 298.1416, found 298.1416.

EXAMPLE 12

The procedures in Example 7 were followed. The product was purified directly on a silica gel column, eluting with 1:1=ethyl acetate:hexane. 7.0 mg of the product was obtained in 39% yield ($R_f$=0.35 in 1:1=EA:Hx, white solid). $^1$H NMR (300 MHz, CDCl$_3$, ppm): δ 6.85(2H, dt, J=7.2, 15.6 Hz), 5.84(2H, dt, J=1.5, 15.6 Hz), 4.26(4H, m), 3.75 (4H, m), 3.67(4H, s), 2.23(4H, m), 1.45(4H, m). $^{13}$C NMR (75 MHz, CDCl$_3$, ppm): δ 166.5, 149.2, 122.1, 71.0, 69.4, 64.0, 31.2, 26.3. HRMS (EI) calcd for C$_{16}$H$_{24}$O$_6$ 312.1573, found 312.1584.

EXAMPLE 13

The procedures in Example 7 were followed. The product was purified directly on a silica gel column, eluting with 1:1=ethyl acetate:hexane. 12.0 mg of the product was obtained in 63% yield ($R_f$=0.35 in 1:1=EA:Hx, white solid). $^1$H NMR (300 MHz, CDCl$_3$, ppm): δ 6.92(2H, dt, J=7.2, 15.6 Hz), 5.83(2H, dt, J=1.5, 15.6 Hz), 4.28(4H, m), 3.73 (4H, m), 3.66(4H, s), 2.24(4H, m), 1.48(4H, m), 1.24(2H, m). $^{13}$C NMR (75 MHz, CDCl$_3$, ppm): δ 166.7, 149.4, 121.9, 71.2, 69.5, 64.1, 32.2, 27.8, 27.7. HRMS (EI) calcd for C$_{17}$H$_{26}$O$_6$ 326.1729, found 326.1732.

EXAMPLE 14

The procedures in Example 7 were followed. The product was purified directly on a silica gel column, eluting with 1:1=ethyl acetate:hexane. 29.4 mg of the product was obtained in 59% yield ($R_f$=0.40 in 1:1=EA:Hx, colorless liquid). $^1$H NMR (300 MHz, CDCl$_3$, ppm): δ 6.98(2H, dt, J=6.9, 15.6 Hz), 5.84(2H, dt, J=1.5, 15.6 Hz), 4.29(4H, m), 3.74(4H, m), 3.68(4H, s), 2.21(4H, dq, J=1.5, 6.6 Hz), 1.50(4H, m), 1.29(4H, m). $^{13}$C NMR (75 MHz, CDCl$_3$, ppm): δ 166.7, 149.8, 121.5, 71.2, 69.6, 64.0, 31.2, 27.3, 26.9. HRMS (EI) calcd for C$_{18}$H$_{28}$O$_6$ 340.1886, found 340.1893.

EXAMPLE 15

The procedures in Example 7 were followed. The product was purified directly on a silica gel column, eluting with 1:2=ethyl acetate:hexane. 31.3 mg of the product was isolated in 55% yield. ($R_f$=0.55 in 1:1=EA:Hx, colorless liquid). $^1$H NMR (300 MHz, CDCl$_3$, ppm): δ 6.95(2H, dt, J=7.2, 15.6 Hz), 5.81(2H, dt, J=1.5, 15.6 Hz), 4.26(4H, m), 3.70(4H, m), 3.65(4H, s), 2.20 (4H, m), 1.44(4H, m), 1.23(12H, m). $^{13}$C NMR (75 MHz, CDCl$_3$, ppm): δ 166.8, 150.2, 121.4, 71.1, 69.8, 64.0, 32.2, 29.1, 28.9, 28.4, 27.7. HRMS (EI) calcd for C$_{22}$H$_{36}$O$_6$ 396.2512, found 396.2507.

EXAMPLE 16

The procedures in Example 7 were followed. The product was purified directly on a silica gel column, eluting with 1:1=ethyl acetate:hexane. 9.0 mg of the product was isolated in 50% yield. ($R_f$=0.35 in 1:1=EA:Hx, colorless liquid). $^1$H NMR (300 MHz, CDCl$_3$, ppm): δ 6.83(1H, dt, J=6.9, 15.6 Hz), 6.71(1H, dd, J=9.6, 15.6 Hz), 5.81(2H, dt, J=1.5, 15.6 Hz), 4.36(2H, m), 4.13(2H, m), 3.73(4H, m), 3.67(4H, s), 2.35 (1H, m), 2.25(2H, m), 1.79(1H, m), 1.50(1H, m)1.04 (3H, d, J=6.9). $^{13}$C NMR (75 MHz, CDCl$_3$, ppm): δ 166.7, 166.5, 153.0, 148.4, 123.0, 121.6, 70.7, 70.5, 69.2, 69.2, 63.8, 63.8, 37.2, 33.1, 30.7, 21.1. HRMS (EI) calcd for C$_{16}$H$_{24}$O$_6$ 312.1573, found 312.1581.

EXAMPLE 17

The procedures in Example 7 were followed. The product was purified directly on a silica gel column, eluting with 1:1=ethyl acetate:hexane. 7.0 mg of the product was isolated in 37% yield. ($R_f$=0.35 in 1:1=EA:Hx, colorless liquid). $^1$H NMR (300 MHz, CDCl$_3$, ppm): δ 6.91(2H, m), 5.81(2H, d, J=15.6 Hz), 4.20(4H, m), 3.72(4H, m), 3.67(4H, s), 2.20(4H, m), 1.5–1.3(3H, m), 0.95(3H, d, J=6.6 Hz). $^{13}$C NMR (75 MHz, CDCl$_3$, ppm): δ 166.5, 149.3, 148.3, 122.8, 121.9, 71.1, 70.1, 69.4, 69.3, 64.1, 39.2, 33.5, 31.3, 29.1, 20.6. HRMS (EI) calcd for C$_{17}$H$_{26}$O$_6$ 326.1729, found 326.1728.

EXAMPLE 18

The procedures in Example 7 were followed. This time 8 mol % of catalyst 2 was used. The product was purified directly on a silica gel column, eluting with 1:10=ethyl acetate:hexane. 25.4 mg of the product was isolated in 59% yield. ($R_f$=0.5 in 1:5=EA:Hx, colorless liquid). ). $^1$H NMR (300 MHz, CDCl$_3$, ppm): δ 5.60(2H, m), 5.33(2H, dd, J=8.1, 15.9 Hz), 5.13(2H, m) 2.10(2H, m), 2.00(6H, s), 1.60(2H, m), 1.50(2H, m), 1.40(2H, m), 1.2(24H, m). $^{13}$C NMR (75 MHz, CDCl$_3$, ppm): δ 170.5, 134.8, 128.9, 75.5, 34.4, 32.1, 29.8, 29.6, 29.2, 29.1, 28.6, 28.2, 24.9, 21.8. HRMS (EI) calcd for C$_{26}$H$_{44}$O$_4$ 420.3240, found 420.3247.

EXAMPLE 19

The procedures in Example 18 were followed using the same reactants as Example 25 except that the cyclic olefin heptene was used instead of dodecene., and 7 mol % of catalyst 2 was used. The product was purified directly on a silica gel column, eluting with 1:10=ethyl acetate:hexane to provide an 84% yield.

EXAMPLE 20

The procedures in Example 18 were followed using the same reactants except that the acyclic diene was replaced with the cyclized diene diol having the following formula:

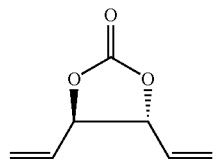

The product was purified directly on a silica gel column, eluting with 1:10=ethyl acetate:hexane to provide a 52% yield of the macrocycle having the following formula:

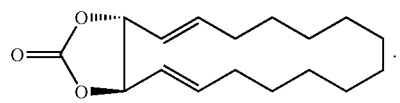

EXAMPLE 21

The procedures in Example 20 were followed using the same reactants except that the cyclic olefin dodecene was replaced with heptene. The product was purified directly on a silica gel column, eluting with 1:10=ethyl acetate:hexane to provide a 52% yield of the macrocycle having the following formula:

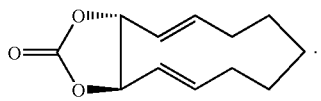

The substrates of Example 7 (also Example 8) and of Example 9 (also Example 10) gave 18- to 26-membered macrocycles with moderate yields (Table 2, entries 7–10). The best yields for ring expansion with cycloalkenes were obtained when the bis-acylate substrate of Example 11 (also in Examples 12–17) having linker oxygen atoms was used (Table 2, entries 11–17). Even thought the substrates of Examples 9–10 and of Example 11–17 have the same number of linker units, the presence of additional oxygen atoms in the Example 11–17 substrate that are less conformationally constraining than carbon linker atoms favors the formation of the desired macrocycle products. With the best substrate identified, various cycloalkenes were screened to create a family of macrocycles (Table 2, entries 11–21). For cyclopentene and cycloheptene, 5 equiv. of cycloalkenes was used since the rates of the ring opening were slower than for cyclooctene. Higher concentrations of cyclopentene and cycloheptene resulted in significant side reactions and did not increase the yields of the desired product. The reaction with cyclohexene gave the poorest yield even though one might have expected a yield comparable if not better than for cyclopentene. However, cyclohexene requires a different mode of the ring expansion. Since cyclohexene will not undergo olefin metathesis reactions with catalyst 2, the initial step is the formulation of the enoic carbene, [Ru=CO$_2$R] in situ, which can ring-open cyclohexene. Since the enoic carbene is less stable than the catalyst 2, fewer catalytic turnovers are expected (Table 2, entry 12, tert butyl silane, "TBS"). Substituted cycloalkenes reacted in a similar way to unsubstituted cycloalkenes to produce substituted macrocycles (Table 2, entries 17–19). Although the bis-allylic acetate of Example 19 can undergo self-metathesis, its reaction with ring-opened cyclododecene was more favored. In that case, two potentially polymerizable substrates reacted to form the ring-expansion product. Furthermore substituted cyclic dienes reacted in a similar way to acyclic dienes to produce substituted macrocycles comprising the cyclic diene structure (Table 2, entries 20 and 21).

TABLE 2

| Entry | Substrates | Ring Size[a] (cycloalkene) | Ring Product[b] | Yield (%) |
|---|---|---|---|---|
| 7 | | 8 | | 45 |
| 8 | Same substrate as 14 | 12 | | 54 |
| 9 | | 8 | | 47 |
| 10 | Same Substrate as 16 | 12 | | 42 |

TABLE 2-continued

| Entry | Substrates | Ring Size[a] (cycloalkene) | Ring Product[b] | Yield (%) |
|---|---|---|---|---|
| 11 | (diacrylate of diethylene glycol) | 5 | (macrocycle) | 52 |
| 12 | Same Substrate as 18 | 6 | (macrocycle) | 39 |
| 13 | Same Substrate as 18 | 7 | (macrocycle) | 63 |
| 14 | Same Substrate as 18 | 8 | (macrocycle) | 59 |
| 15 | Same Substrate as 18 | 12 | (macrocycle) | 55 |
| 16 | Same Substrate as 18 | methylcyclopentene | (macrocycle with CH₃) | 50 |
| 17 | Same Substrate as 18 | methylcyclohexene | (macrocycle with CH₃) | 37 |

TABLE 2-continued

| Entry | Substrates | Ring Size[a] (cycloalkene) | Ring Product[b] | Yield (%) |
|---|---|---|---|---|
| 18 | (structure with two OAc and two vinyl groups) | 12 | (macrocycle with two OAc) | 59 |
| 19 | (structure with two OAc and two vinyl groups) | 7 | (macrocycle with two OAc) | 84 |
| 20 | (cyclic carbonate with two vinyl groups) | 12 | (macrocycle with cyclic carbonate) | 59 |
| 21 | (cyclic carbonate with two vinyl groups) | 7 | (macrocycle with cyclic carbonate) | 84 |

[a]Reactions were performed using catalyst 2 (5 mol %) in refluxing $CH_2Cl_2$ (5 mM) under an atmosphere of argon.
[b]Ring size: 5, cyclopentene; 6, cyclohexene; 7, cycloheptene; 8, cyclooctene; 12 cyclododecene.
[c]Only (E)-isomers were observed by $^1H$ NMR.
[d]Isolated yields. No starting material remained except in Examples 12 and 17.

Ring Expansion of Cyclic Olefin and Bis-Acrylate Dienes via Sequential ROM, CM and RCM with Catalyst (2) to form Macrocycles Other acyclic dienes that undergo selective cross metathesis can serve as the acyclic diene reactant in the ring expansion reactions described above to produce macrocycles. One such substrate having no oxygen atoms in the linker chain yielded 48% of the desired single insertion macrocycle product under conditions similar to the corresponding Example 18 (Table 2, entry 18, above) acyl protected acrylate reaction. Using the tandem catalysis described above and olefin hydrogenation, a macrocycle saturated diketone was obtained in a one pot process. Namely, a bis-vinyl ketone diene having a ten-carbon linker chain without any oxygen atoms in the linker chain was reacted with the cycloolefin octene in a one-pot reaction followed by hydrogenation at 50 psi yielded a 22-membered saturated cyclic dione. See Scheme 3 and Example 22, below.

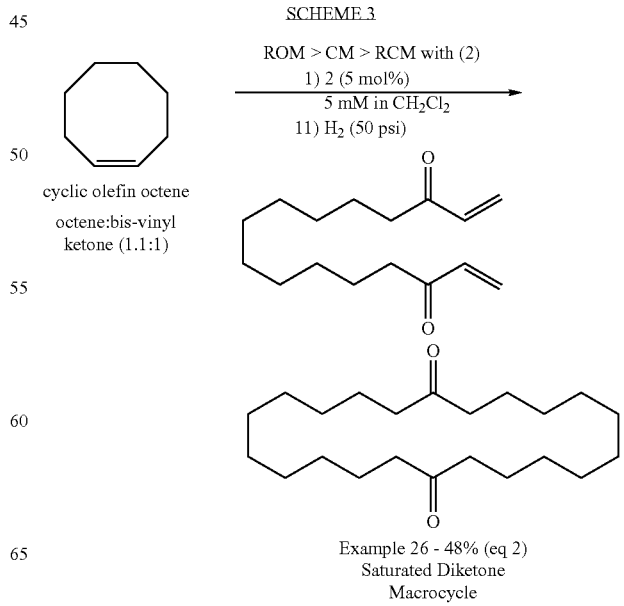

SCHEME 3

ROM > CM > RCM with (2)
1) 2 (5 mol%)
5 mM in $CH_2Cl_2$
11) $H_2$ (50 psi)

cyclic olefin octene
octene:bis-vinyl ketone (1.1:1)

Example 26 - 48% (eq 2)
Saturated Diketone Macrocycle

EXAMPLE 22

The procedures of Example 18 were followed. After metathesis reaction was done, the pot was pressured up with 50 psi hydrogen gas, and ran for overnight. The product was purified directly on a silica gel column, eluting with 1:10=ethyl acetate:hexane. 13.0 mg of the product was isolated in 48% yield. ($R_f$=0.45 in 1:4=EA:Hx, white solid). $^1$H NMR (300 MHz, CDCl$_3$, ppm): δ 2.39(8H, t, J=6.9 Hz), 1.58(8H, m), 1.23(24H, m). $^{13}$C NMR (75 MHz, CDCl$_3$, ppm): δ 212.5, 41.6, 29.1, 29.0,28.8, 24.1. HRMS (EI) calcd for C$_{22}$H$_{40}$O$_2$ 336.3028, found 336.3024.

In summary, Examples 1–22, demonstrated the synthesis of various macrocycles by a ring-expansion method according to the invention using catalyst 2. The examples show that varying the concentration and the stoichiometry of the cyclic olefin controlled the product distribution. Although the yields of the ring expansion products are moderate in the illustrated examples, this methodology provides an easy access to a variety of macrocycles whose ring sizes can be adjusted by using readily available cyclic olefins to expand the rings of dienes having two terminal olefinic groups.

We claim:

1. A method for synthesizing a macrocycle by ring expansion of a cyclic olefin, comprising three metathesis steps in the following order:
   (i) a ring-opening metathesis (ROM) reaction step of the cyclic olefin;
   (ii) a cross metathesis (CM) step reaction with a diene having two terminal olefinic groups; and
   (iii) a ring closure metathesis (RCM) reaction step;
   wherein steps (i)–(iii) are carried out in the present of a catalytically effective amount of an olefin metathesis catalyst under reaction conditions effective to allow each of the three metathesis reactions to occur.

2. The method of claim 1, wherein the reaction conditions of step (ii) or (iii) comprise carrying out the metathesis in the presence of a catalytically effective amount of the olefin metathesis catalyst of step (i).

3. The method of claim 2, wherein the reaction conditions of steps (ii) and (iii) comprise carrying out the CM and RCM metathesis in the presence of a catalytically effective amount of the olefin metathesis catalyst of step (i).

4. The method of claim 1, wherein the diene having two terminal olefinic groups is generated in situ from a cyclic diene via a ring-opening cross metathesis (ROCM) reaction.

5. The method of claim 1, wherein the intermediate from each step is not isolated before proceeding to the next step.

6. The method of claim 5, wherein following step (iii) the macrocycle is isolated and purified.

7. The method of claim 1, wherein the macrocycle is further modified.

8. The method of claim 7, wherein the further modification comprises removing protecting groups, hydrogenating olefinic bonds, hydrogenating carbonyl groups, substituting a second cyclic olefin residue into the alternating copolymer by a cross metathesis insertion to replace olefinic residues from the polyolefin intermediate, or combinations thereof.

9. The method of claim 1, wherein the olefin metathesis catalyst is a Group 8 transition metal complex having the structure of formula (I)

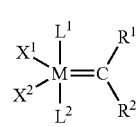

in which:
M is a Group 8 transition metal;
L$^1$ and L$^2$ are neutral electron donor ligands;
X$^1$ and X$^2$ are anionic ligands; and
R$^1$ and R$^2$ are independently selected from hydrogen, hydrocarbyl, substituted hydrocarbyl, heteroatom-containing hydrocarbyl, substituted heteroatom-containing hydrocarbyl, and functional groups;
wherein any two or more of X$^1$, X$^2$, L$^1$, L$^2$, R$^1$, and R$^2$ can be taken together to form a cyclic group, and further wherein any one of X$^1$, X$^2$, L$^1$, L$^2$, R$^1$, and R$^2$ can be attached to a support.

10. The method of claim 9, wherein M is Ru or Os.

11. The method of claim 10, wherein M is Ru.

12. The method of claim 11, wherein:
R$^1$ is hydrogen, and R$^2$ is selected from C$_1$–C$_{20}$ alkyl, C$_2$–C$_{20}$ alkenyl, and C$_5$–C$_{20}$ aryl, optionally substituted with one or more moieties selected from C$_1$–C$_6$ alkyl, C$_1$–C$_6$ alkoxy, and phenyl;
L$^1$ and L$^2$ are independently selected from phosphine, sulfonated phosphine, phosphite, phosphinite, phosphonite, arsine, stibine, ether, amine, amide, imine, sulfoxide, carboxyl, nitrosyl, pyridine, substituted pyridine, imidazole, substituted imidazole, pyrazine, and thioether; and
X$^1$ and X$^2$ are independently selected from hydrogen, halide, C$_1$–C$_{20}$ alkyl, C$_5$–C$_{20}$ aryl, C$_1$–C$_{20}$ alkoxy, C$_5$–C$_{20}$ aryloxy, C$_2$–C$_{20}$ alkoxycarbonyl, C$_6$–C$_{20}$ aryloxycarbonyl, C$_2$–C$_{20}$ acyl, C$_2$–C$_{20}$ acyloxy, C$_1$–C$_{20}$ alkylsulfonato, C$_5$–C$_{20}$ arylsulfonato, C$_1$–C$_{20}$ alkylsulfanyl, C$_5$–C$_{20}$ arylsulfanyl, C$_1$–C$_{20}$ alkylsulfinyl, or C$_5$–C$_{20}$ arylsulfinyl, any of which, with the exception of hydrogen and halide, are optionally further substituted with one or more groups selected from halide, C$_1$–C$_6$ alkyl, C$_1$–C$_6$ alkoxy, and phenyl.

13. The method of claim 12, wherein:
R$^2$ is selected from phenyl, vinyl, methyl, isopropyl, and t-butyl;
L$^1$ and L$^2$ are phosphines of the formula PR$^5$R$^6$R$^7$, where R$^5$, R$^6$, and R$^7$ are each independently aryl or C$_1$–C$_{10}$ alkyl; and
X$^1$ and X$^2$ are independently selected from halide, CF$_3$CO$_2$, CH$_3$CO$_2$, CFH$_2$CO$_2$, (CH$_3$)$_3$CO, (CF$_3$)$_2$(CH$_3$)CO, (CF$_3$)(CH$_3$)$_2$CO, PhO, MeO, EtO, tosylate, mesylate, and trifluoromethanesulfonate.

14. The method of claim 13, wherein:
R$^2$ is phenyl or vinyl;
L$^1$ and L$^2$ are selected from tricyclohexylphosphine, tricyclopentylphosphine, triisopropylphosphine, triphenylphosphine, diphenylmethylphosphine, and phenyldimethylphosphine; and
X$^1$ and X$^2$ are halide.

15. The method of claim 14, wherein:
R$^2$ is phenyl;
L$^1$ and L$^2$ are the same, and are selected from tricyclohexylphosphine and tricyclopentylphosphine; and
X$^1$ and X$^2$ are chloro.

16. The method of claim 1, wherein the cyclic olefin monomer has the structure of formula (IV):

$$\begin{array}{c} R^{27} \diagdown \overset{X^4}{\phantom{X}} \diagup R^{27B} \\ R^{27A} \phantom{XX} R^{27C} \\ \phantom{XXX} \\ R^{15} \phantom{XX} R^{16} \end{array} \quad (IV)$$

wherein:
- $X^4$ is a one-atom to five-atom linkage;
- one of $R^{15}$ and $R^{16}$ is hydrogen and the other is selected from hydrogen, hydrocarbyl, substituted hydrocarbyl, heteroatom-containing hydrocarbyl, substituted heteroatom-containing hydrocarbyl, and -(L)$_v$-Fn wherein v is zero or 1, L is hydrocarbylene, substituted hydrocarbylene and/or heteroatom-containing hydrocarbylene, and Fn is a protected or unprotected functional group; and
- $R^{27}$, $R^{27A}$, $R^{27B}$, and $R^{27C}$ are independently selected from hydrogen, hydrocarbyl, substituted hydrocarbyl, heteroatom-containing hydrocarbyl, and substituted heteroatom-containing hydrocarbyl, and -(L)$_v$-Fn, and further wherein any two of $R^{27}$, $R^{27A}$, $R^{27B}$, and $R^{27C}$ may be taken together to form a cyclic structure, such that the olefin monomer is bicyclic, with the proviso that when the olefin monomer is bicyclic, then $X^4$ is a one-atom or two-atom linkage.

17. The method of claim 16, wherein $R^{15}$, $R^{16}$, $R^{27}$, $R^{27A}$, $R^{27B}$, and $R^{27C}$ are each hydrogen atoms.

18. The method of claim 17, wherein $R^{27A}$ and $R^{27C}$ are hydrogen, $R^{27}$ is -(L)$_v$-Fn wherein v is zero and -Fn is —$X^{3A}$—$(R^{18})_n$, and $R^{27B}$ is -(L)$_v$-Fn wherein v is zero and -Fn is —$X^3$—$(R^{17})_m$, and further wherein $X^3$ and $X^{3A}$ are directly or indirectly linked.

19. The method of claim 16, wherein the cyclic olefin has the structure of formula VII $$\begin{array}{c} \phantom{X} X^4 \\ R^{15} \diagdown \phantom{X} \diagup X^{3A}{-}(R^{18})_n \\ \phantom{XX} | \\ \phantom{XX} [P^*]_k \\ R^{16} \diagup \phantom{X} \diagdown X^3 \\ \phantom{XXXX} | \\ \phantom{XXX} (R^{17})_m \end{array} \quad (VII)$$

in which:
- $X^4$ is a one-atom or two-atom linkage;
- $X^3$ and $X^{3A}$ are independently N, O, or S;
- k is zero or 1;
- m and n are independently zero or 1;
- P* is a heteroatom-protecting group;
- $R^{17}$ and $R^{18}$ are independently selected from hydrogen, hydrocarbyl, substituted hydrocarbyl, heteroatom-containing hydrocarbyl, substituted heteroatom-containing hydrocarbyl, and amino protecting groups, wherein $R^{17}$ and $R^{18}$ may be taken together to form a cyclic group, with the provisos that:
  - when $X^3$ is O or S, then m is zero;
  - when $X^{3A}$ is O or S, then n is zero;
  - when $X^3$ is N, then m is 1; and
  - when $X^{3A}$ is N, then n is 1.

20. The method of claim 16, wherein $R^{27A}$ and $R^{27C}$ of formula (IV) are hydrogen, in which case the cyclic olefin has the structure of formula (VIIa)

$$\begin{array}{c} R^{27} \diagdown \overset{X^4}{\phantom{X}} \diagup R^{27B} \\ \phantom{XXX} \\ R^{25} \phantom{XX} R^{26} \end{array} \quad (VIIa)$$

wherein $X^4$, $R^{27}$, and $R^{27B}$ are as defined in claim 16, and $R^{25}$ and $R^{26}$ are defined as $R^{15}$ and $R^{16}$ are defined in claim 16.

21. The method of claim 20, wherein $X^4$ is $C_1$ to $C_5$ alkylene, or substituted $C_1$ to $C_5$ alkylene.

22. The method of claim 21, wherein the substituted $C_1$ to $C_5$ alkylene is substituted by at least one alcohol or protected alcohol group.

23. The method of claim 22, wherein an alcohol group is protected by a TBS group, an acyl group, or a tetrahydropyran group.

24. The method of claim 20, wherein the cyclic olefin monomer is selected from cyclopentene, 3-methylcyclopentene, 4-methylcyclopentene, 3-t-butyldimethyl-silyloxycyclopentene, 4-t-butyl-dimethylsilyloxycyclopentene, cyclohexene, 3-methylcyclohexene, 4-methyl-cyclohexene, 3-t-butyldimethylsilyloxycyclohexene, 4-t-butyldimethyl-silyloxycyclohexene, cycloheptene, 3-methylcycloheptene, 4-methylcycloheptene, 5-methylcyclo-heptene, 3-t-butyldimethylsilyloxy-cycloheptene, 4-t-butyldimethylsilyloxycycloheptene, 5-t-butyldimethylsilyloxycycloheptene, cyclooctene, 3-methylcyclooctene, 4-methylcyclooctene, 5-methylcyclooctene, 3-t-butyldimethyl-silyloxycyclooctene, 4-i-butyldimethylsilyloxy-cyclooctene, 5-t-butyldimethylsilyloxycyclooctene, cyclononene, 3-methylcyclononene, 4-methylcyclononene, 5-methylcyclononene, 6-methylcyclo-nonene, 3-t-butyldimethyl-silyloxycyclononene, 4-t-butyldimethylsilyloxycyclononene, 5-t-butyl-dimethylsilyloxycyclononene, 6-t-butyldimethylsilyloxycyclononene, cyclodecene, 3-methylcyclo-decene, 4-methylcyclo-decene, 5-methylcyclodecene, 6-methylcyclodecene, 3-t-butyldimethylsilyl-oxycyclodecene, 4-t-butyldimethylsilyloxycyclononene, 5-t-butyldimethylsilyloxycyclodecene, 6-t-butyldimethylsilyloxycyclodecene, cycloundecene, 3-methylcycloundecene, 4-methylcyclo-undecene, 5-methylcycloundecene, 6-methylcycloundecene, 7-methylcycloundecene, 3-t-butyl-dimethylsilyloxycycloundecene, 4-t-butyldimethylsilyloxycycloundecene, 5-t-butyldimethyl-silyloxycycloundecene, 6-t-butyldimethylsilyloxycycloundecene, 7-t-butyldimethylsilyloxycycloundecene, cyclododecene, 3-methylcyclododecene, 4-methylcyclododecene, 5-methylcyclododecene, 6-methylcyclododecene, 7-methylcyclododecene, 3-t-butyldimethylsilyloxycyclododecene, 4-t-butyldimethyl-silyloxycyclododecene, 5-t-butyldimethylsilyloxy-cyclododecene, 6-t-butyldimethylsilyloxy-cyclododecene, and 7-t-butyldimethylsilyloxycyclododecene.

25. The method of claim 24, wherein the cyclic olefin monomer is selected from cyclopentene, 3-methylcyclopentene, 3-t-butyldimethylsilyloxycyclopentene, cyclohexene, 4-methyl-cyclohexene, 4-t-butyldimethylsilyloxycyclohexene, cycloheptene, cyclooctene, 5-methylcyclo-octene, 5-t-butyldimethylsilyloxycyclooctene, cyclononene, and cyclododecene.

26. The method of claim 1, wherein the two terminal olefinic groups of the diene are joined by a hydrocarbylene linker group comprising 6–30 carbon atoms, wherein the carbon atoms of the linker group may be substituted or unsubstituted and the linker group may be interrupted by up to 6 hetero atoms selected from O, S and N, and wherein two or more constituents on the chain may be linked to form an additional cyclic group.

27. The method of claim 26, wherein the two terminal olefinic groups of the diene taken together with adjacent atoms of the linker group form a bis-acrylate acyclic diene compound, a bis-vinyl ketone acyclic diene compound, or a bis-allylic acetate acyclic diene compound.

28. The method of claim 27, wherein the linker group is hydrocarbylene, substituted hydrocarbylene, heteroatom-containing hydrocarbylene, or substituted heteroatom-containing hydrocarbylene linker, and two or more constituents on adjacent atoms of the chain may be linked to form an additional cyclic group, and wherein up to 6 carbon atoms of the linker group may be substituted by functional groups, or protected functional groups.

29. The method of claim 28, wherein functional groups or protected functional groups substituted on the carbon atoms of the linker group are independently selected from halogen, alcohol, oxo, thiol, —SO$_3$—H, a substituted —SO$_2$— group, amino, substituted amino, or combinations thereof.

30. The method of claim 29, wherein the acyclic diene is selected from formula (VIIb) and (VIIc) as follows:

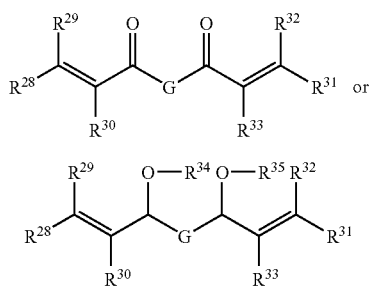

wherein:
$R^{28}$, $R^{29}$, $R^{31}$, and $R^{32}$ are each independently hydrogen or a substituent that does not interfere with olefin cross metathesis,
$R^{30}$ and $R^{33}$ are each independently hydrogen or a leaving group that that does not interfere with olefin cross metathesis,
$R^{34}$ and $R^{35}$ are each independently hydrogen, a non-acyl alcohol protecting group, or an acyl group, and
G is hydrocarbylene linker group comprising 6–30 carbon atoms, wherein the carbon atoms of the linker group may be substituted or unsubstituted and the linker group may be interrupted by up to 6 hetero atoms selected from O, S and N, and wherein two or more constituents on the chain may be linked to form an additional cyclic group.

31. The method of claim 30, wherein G is a linker chain constructed by 2 to 24 linked —$X^7$— groups, wherein each occurrence of $X^7$ in the linker chain is independently selected from $CR^{36}R^{37}$, O, S, or $NR^{38}$, and $R^{36}$, $R^{37}$, and $R^{38}$ are independently selected from hydrogen, substituted hydrocarbyl, heteroatom-containing hydrocarbyl, substituted heteroatom-containing hydrocarbyl, functional groups and protected functional groups, wherein up to 6 pairs of $CR^{36}R^{37}$ groups of the linker chain may be independently interrupted by an O, S, or $NR^{38}$ group.

32. The method of claim 31, wherein the acyclic diene has a structure selected from the following formulae:

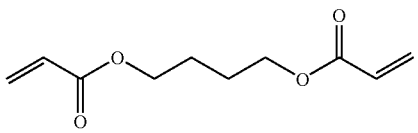

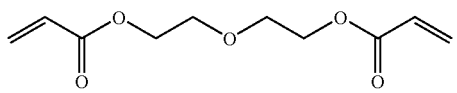

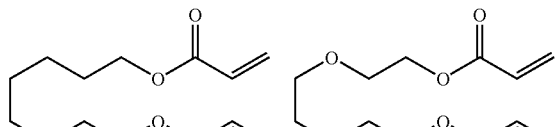

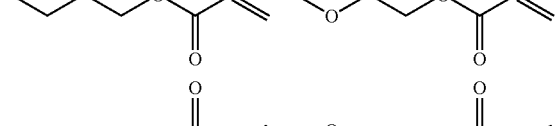

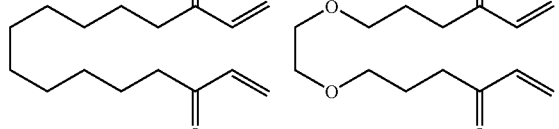

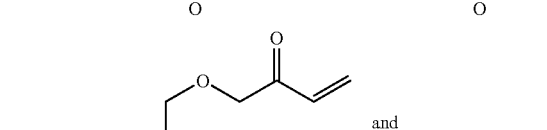

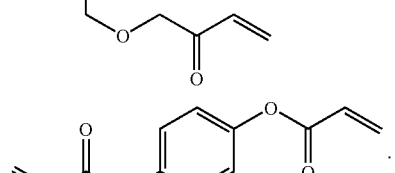

and

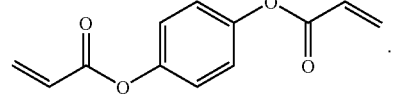

33. The method of claim 1, wherein the macrocycle has a structure selected from the following formulae:

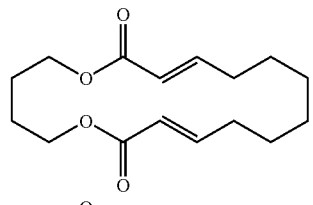

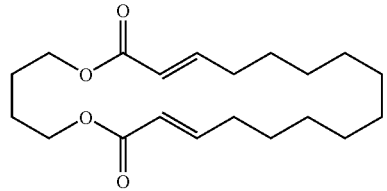

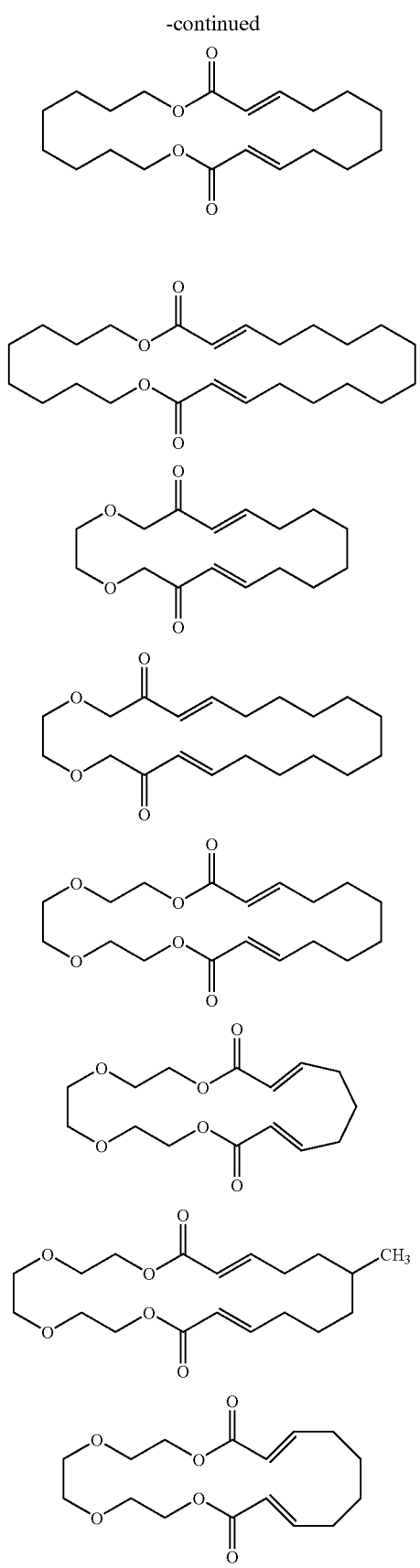

-continued

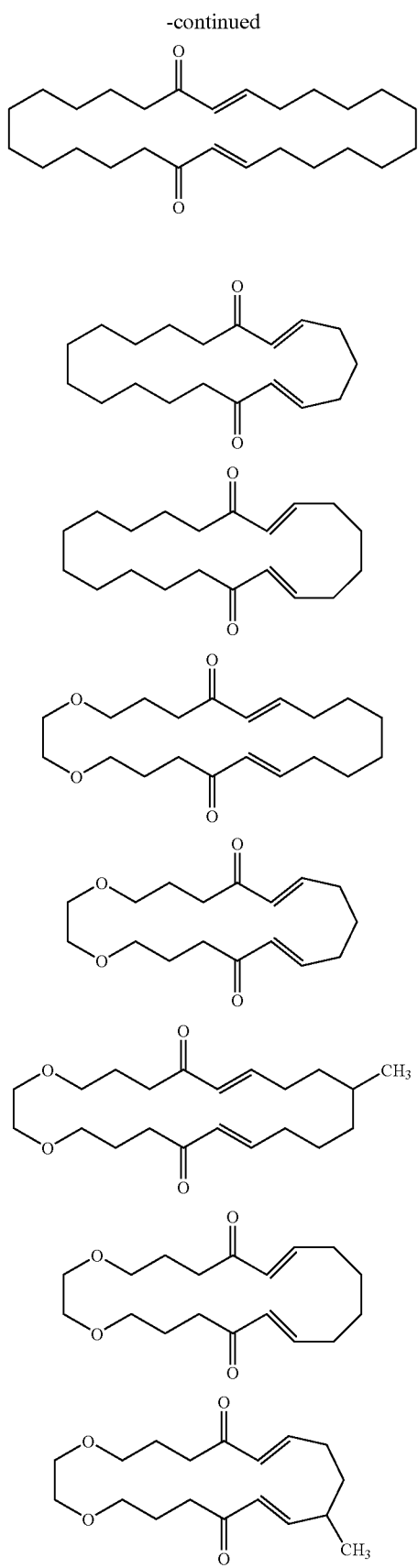

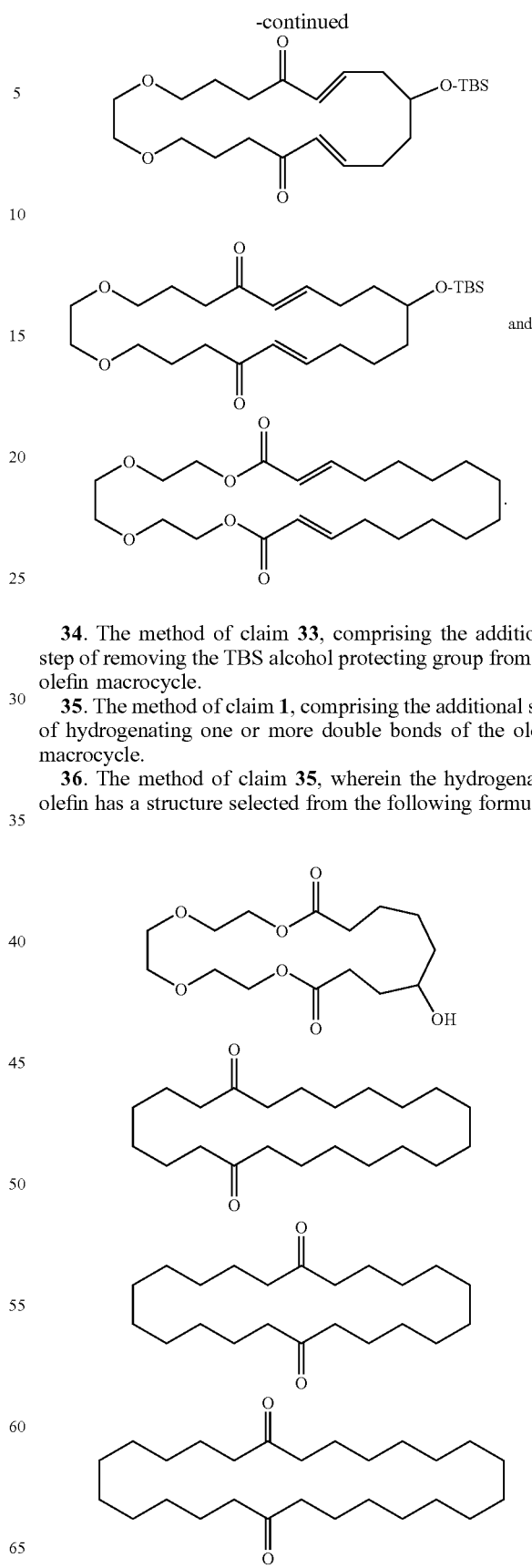

34. The method of claim 33, comprising the additional step of removing the TBS alcohol protecting group from the olefin macrocycle.

35. The method of claim 1, comprising the additional step of hydrogenating one or more double bonds of the olefin macrocycle.

36. The method of claim 35, wherein the hydrogenated olefin has a structure selected from the following formulae:

-continued

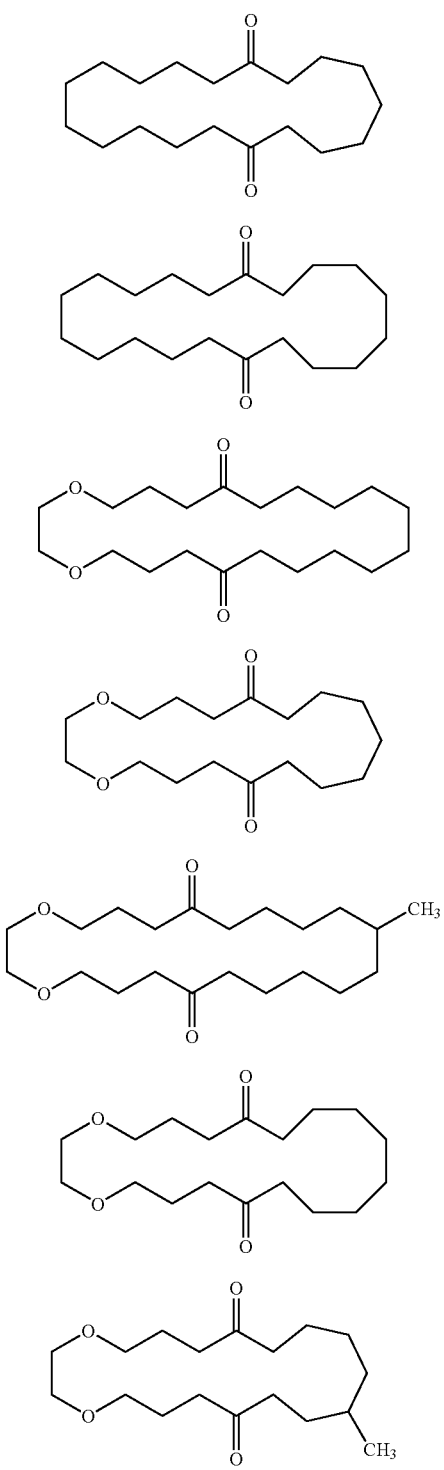

-continued

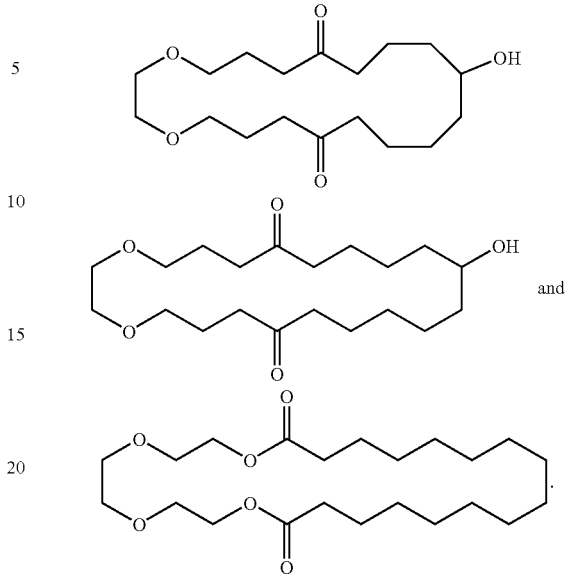

37. The method of claim 1, wherein the diene having two terminal olefinic groups is present in the reaction solution in a molar concentration range from 0.003 to 0.010.

38. The method of claim 1, wherein the diene having two terminal olefinic groups is present in the reaction solution in a molar concentration range from 0.005 to 0.007.

39. The method of claim 38, wherein the metathesis catalyst is present in 0.01 to 0.20 molar equivalents with respect to the diene.

40. The method of claim 38, wherein the metathesis catalyst is present in 0.02 to 0.10 molar equivalents with respect to the diene.

41. The method of claim 38, wherein the metathesis catalyst is present in 0.04 to 0.06 molar equivalents with respect to the diene.

42. The method of claim 38, wherein the metathesis catalyst is present in 0.05 molar equivalents with respect to the diene.

43. The method of claim 1, wherein the process is carried out in an organic solvent.

44. The method of claim 43, wherein the organic solvent is selected from toluene, dichloromethane, dichloroethane, and combinations thereof.

45. The method of claim 38, wherein the cyclic olefin is present in a molar ratio from 1:1 to 25:1 with respect to the diene.

46. The method of claim 38, wherein the cyclic olefin is present in a molar ratio from 1.1:1 to 5:1 with respect to the diene.

47. The method of claim 38, wherein the cyclic olefin is present in a molar ratio from 1.1:1 to 2:1 with respect to the diene.

* * * * *

UNITED STATES PATENT AND TRADEMARK OFFICE
CERTIFICATE OF CORRECTION

PATENT NO. : 7,034,096 B2 Page 1 of 1
APPLICATION NO. : 10/371196
DATED : April 25, 2006
INVENTOR(S) : Tae-Lim Choi et al.

It is certified that error appears in the above-identified patent and that said Letters Patent is hereby corrected as shown below:

On Title Page Item (54) col. 1
Please delete "RING-EXPANSION OF CYCLIC OLEFINS METATHESIS REACTIONS WITH AN ACYCLIC DIENE" and replace it with -- RING-EXPANSION OF CYCLIC OLEFINS BY OLEFIN METATHESIS REACTIONS WITH AN ACYCLIC DIENE--

Signed and Sealed this

Twenty-first Day of November, 2006

JON W. DUDAS
*Director of the United States Patent and Trademark Office*